(12) United States Patent
Seto

(10) Patent No.: US 7,866,884 B2
(45) Date of Patent: Jan. 11, 2011

(54) X-RAY CT APPARATUS, METHOD OF ALIGNING PHANTOM, AND PHANTOM RETAINING TOOL

(75) Inventor: Hiromitsu Seto, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/626,630

(22) Filed: Jan. 24, 2007

(65) Prior Publication Data

US 2007/0172025 A1 Jul. 26, 2007

(30) Foreign Application Priority Data

Jan. 26, 2006 (JP) ............... 2006-017152

(51) Int. Cl.
*G01D 18/00* (2006.01)
(52) U.S. Cl. .......................... 378/207; 378/18
(58) Field of Classification Search ...................... 378/4, 378/18, 207
See application file for complete search history.

(56) References Cited

U.S. PATENT DOCUMENTS

| | | | | |
|---|---|---|---|---|
| 4,117,337 A | * | 9/1978 | Staats | 378/17 |
| 4,296,329 A | * | 10/1981 | Mirabella | 250/491.1 |
| 4,558,458 A | * | 12/1985 | Katsumata et al. | 378/20 |
| 4,580,054 A | * | 4/1986 | Shimoni | 250/363.04 |
| 4,812,983 A | * | 3/1989 | Gullberg et al. | 378/14 |
| 4,897,788 A | * | 1/1990 | King | 378/12 |
| 4,998,268 A | * | 3/1991 | Winter | 378/63 |
| 5,099,505 A | * | 3/1992 | Seppi et al. | 378/65 |

(Continued)

FOREIGN PATENT DOCUMENTS

DE 198 60 524 A1 7/2000

(Continued)

OTHER PUBLICATIONS

Gullberg et al., Reconstruction Algorithm for Fan Beam with a Displaced Center-of-Rotation, IEEE Transactions on Medical Imaging, vol. MI-5, No. 1, Mar. 1986, pp. 23-29.*

(Continued)

*Primary Examiner*—Edward J Glick
*Assistant Examiner*—Alexander H Taningco
(74) *Attorney, Agent, or Firm*—Oblon, Spivak, McClelland, Maier & Neustadt, L.L.P.

(57) ABSTRACT

The present invention comprises a top plate 31 for placing a cylindrical phantom 100, an X-ray tube 22 that generates X-rays, an X-ray detector 23 that detects X-rays transmitted through the phantom 100 placed on a top plate 31, a supporting body drive part 25 that rotates the X-ray tube 22 and X-ray detector 23, a tomographic image data generating part 60 that generates tomographic image data on the phantom 100 based on a results of detecting X-rays by the X-ray detector 23, a calculation processing part 80 that calculates displacement of the cylinder axis J of the phantom 100 relative to the center of rotation (center of scan) by the supporting body drive part 25, based on the tomographic image data, and the angle of gradient of the cylinder axis J relative to the normal direction (direction of slice) of the rotation plane of said rotation, and a monitor 5 that displays the calculated results.

1 Claim, 16 Drawing Sheets

U.S. PATENT DOCUMENTS

| | | | | |
|---|---|---|---|---|
| 5,214,578 | A | * | 5/1993 | Cornuejols et al. .......... 378/207 |
| 5,774,519 | A | * | 6/1998 | Lindstrom et al. ............ 378/18 |
| 6,067,341 | A | * | 5/2000 | Horiuchi ........................ 378/8 |
| 6,198,789 | B1 | * | 3/2001 | Dafni ............................. 378/8 |
| 6,385,280 | B1 | * | 5/2002 | Bittl et al. ..................... 378/16 |
| 6,568,851 | B2 | * | 5/2003 | Saito ........................... 378/207 |
| 6,990,171 | B2 | * | 1/2006 | Toth et al. ..................... 378/16 |
| 2003/0048867 | A1 | * | 3/2003 | Acharya et al. ............... 378/18 |
| 2005/0094771 | A1 | * | 5/2005 | Basu et al. .................. 378/207 |

FOREIGN PATENT DOCUMENTS

| | | | |
|---|---|---|---|
| EP | 1 501 052 A1 | | 1/2005 |
| JP | 2001-314397 | | 11/2001 |
| JP | 2001314397 A | * | 11/2001 |
| WO | WO 97/40766 | | 11/1997 |
| WO | WO 00/07037 | | 2/2000 |

OTHER PUBLICATIONS

Crawford et al., Reconstruction for fan beam with an angular-dependent displaced center-of-rotation, Med Phys, 15 (1), Jan.-Feb. 1968, pp. 67-71.*

Yi Sun et al., A Calibration Method for Misalignment Scanner Geometry in Cone-beam Computed Tomography, School of Electronic and Information Engineering; Dalian University of Technology, Sep. 2005, pp. 1-25.*

* cited by examiner

X-RAY CT APPARATUS, METHOD OF ALIGNING PHANTOM, AND PHANTOM RETAINING TOOL

BACKGROUND OF THE INVENTION

1. Field of the Invention

The present invention relates to X-ray CT (computed tomography) apparatus, a method of aligning the phantom, and a phantom retaining tool, and more specifically relates to technology for aligning the phantom for X-ray CT apparatus.

2. Description of the Related Art

X-ray CT apparatus generates X-rays using an X-ray generator, and the X-rays that transmitted through an object on a bed are detected by an X-ray detector to form X-ray projection data, and it generates 2-dimensional tomographic image data showing the internal morphology of the object by applying a reconstruction processing to the X-ray projection data. Furthermore, with X-ray CT apparatus capable of a so-called helical scan, multiple tomographic image data can be reconstructed with a single scan by conducting a scan by rotation of an X-ray generator and an X-ray detector inside a gantry as the bed is being moved in the direction of the body axis (slice direction) of an object.

In order to obtain high-precision tomographic image data, it is necessary to maintain good performance of the apparatus by calibrating the X-ray CT apparatus. Therefore, it is necessary to adjust the apparatus by evaluating performance when the apparatus is shipped and installed, and even regularly after being put into operation. In addition, noise, contrast scale, spatial resolution, thickness of slice, high-contrast resolution, and low-contrast resolution may be listed as evaluation items.

Evaluation of X-ray CT apparatus is performed by using a pseudo body that simulates the human body, called a phantom, instead of an actual human body. FIG. 1A shows the appearance of the phantom 100. The phantom 100 comprises a cylindrical case 101. The cylinder axis of the case 101 is indicated by a symbol J. This cylinder axis J is the axis of rotational symmetry of the cylindrical body (case 101).

FIG. 1B shows a cross-section 110 of the phantom 100 in an arbitrary slice position (excluding proximity of both ends). The case 101 of the phantom 100 is formed in a hollow center. The interior of the hollow center is filled with a filling 102 such as water.

In order to ensure accuracy of a performance evaluation using a cylindrical phantom 100, the phantom 100 must be placed in a suitable setting position. To that end, the cylinder axis J of the phantom 100 must match the slice direction. Moreover, it is necessary to place a cylinder axis J on the center of the scan (center of rotation of the X-ray generator and X-ray detector), as well as to place the phantom 100 in the center of the examination region.

The process of installing the phantom 100 is as follows. First, a phantom 100 is placed on a bed and tomographic image data is reconstructed. The operator adjusts the window width and/or window level so that an outline of the phantom 100, or in other words, the case 101 is displayed clearly, as the operator observes the image of the displayed tomographic image data (tomographic image). Then, a cross-scale (intersection across the center of the display screen indicates the center of the scan) is superimposed on the tomographic image to be displayed. The operator specifies, by visual measurement, to what degree the center position of the case 101—which is indicated in the tomographic image—is displaced and in which direction from the intersection of the cross-scale. Then, as the setting position of the phantom 100 is moved again, the tomographic image is observed to check the position after the move. This type of serial operation is repeated in order to set the phantom 100 in the targeted position.

A method for detecting the position of a phantom to confirm that the phantom is suitably set is disclosed in Japanese Unexamined Patent Application Publication 2001-314397. The detection method described in this literature comprises: scanning a phantom positioned on the center axis of rotation (center of the scan) of an X-ray imaging system along the body axis with a horizontal view; comparing each of the obtained projection data and the predetermined threshold value to extract the outline shape of the phantom in a 2-dimensional projection image region; and detecting the vertical gradient of the phantom based on the extracted outline shape. In other words, in this conventional method, the posture to install is detected by detecting the gradient of a lateral image (scanogram) of the phantom.

With the conventional method of setting a phantom, because the distance to move the phantom is visually specified by the operator, it is difficult to set a phantom in the targeted position with one attempt of the above-described serial operation, and this serial operation is normally repeated many times. Therefore, the operation of setting a phantom becomes a prolonged process, which is a heavy burden on the operator.

Furthermore, to set a phantom in the targeted position, the position of the phantom must be moved 2-dimensionally. Therefore, it can be relatively quick for a skilled operator to grasp a direction and distance of movement, but for operators who are not as skilled, such an operation is difficult. In addition, this kind of operation depends upon the sense of the operator, and some operators do not improve their skill with experience.

On the other hand, in the invention disclosed in Japanese Unexamined Patent Application Publication 2001-314397, the posture is detected with the assumption that the cylinder axis of the phantom is placed on the center of the scan. Thus, when such a method is used, the operation of matching the cylinder axis of the phantom with the center of the scan must be manually performed beforehand, so time and effort are required. Moreover, these hitherto known inventions had the problem of being unable to confirm whether the phantom is positioned at the center of the scan.

Furthermore, the invention disclosed in Japanese Unexamined Patent Application Publication 2001-314397 uses only the result of lateral scanning of the phantom, so it can detect only the vertical gradient. In the actual positioning operation, the phantom could lean horizontally, but it could not be handled by the existing inventions.

SUMMARY OF THE INVENTION

The objective of the present invention is intended to solve the above-mentioned problems by providing technology that enables a phantom to quickly and easily be aligned, regardless of the level of skill of the operator.

Moreover, another objective of the present invention is intended to provide technology that enables a phantom to be aligned with high precision in a simple alignment operation.

According to the first embodiment of the invention, when aligning a phantom that is set on the top plate of a bed, tomographic image data is generated on the phantom based on the results of detecting X-rays by an X-ray detector. Then, information is calculated regarding displacement of the phantom relative to the center of rotation (center of the scan) of the X-ray generator and the X-ray detector by a rotation drive unit based on the generated tomographic image data. Then, information for alignment of the phantom is displayed based on information regarding the calculated displacement.

According to the first embodiment of the invention, operators can easily obtain information for alignment, based on displacement (misalignment) of the cylinder axis of the phantom relative to the center of the scan. Thus, it becomes possible to quickly and easily align the cylinder axis of the phantom with the center of the scan, regardless of the level of skill of the operator.

According to the second embodiment of the invention, when aligning a phantom that is set on a top plate of a bed, tomographic image data is generated on the phantom based on the results of detecting X-rays by an X-ray detector. Then, information is calculated regarding displacement of the phantom relative to the center of rotation (center of the scan) of the X-ray generator and the X-ray detector by a rotation drive unit based on the generated tomographic image data. Then, the top plate is moved to align the cylinder axis of the phantom with the center of the scan based on information regarding the calculated displacement.

According to the second embodiment of the invention, there is no need to perform a manual operation to align the cylinder axis of the phantom with the center of the scan. Thus, it becomes possible to quickly and easily align a phantom, regardless of the level of skill of the operator.

According to the third embodiment of the invention, when aligning a phantom that is set on a top plate of a bed, tomographic image data is generated on the phantom based on the results of detecting X-rays by an X-ray detector. Then, information is calculated regarding displacement of the phantom relative to the center of rotation (center of the scan) by a rotation drive unit based on the generated tomographic image data. Then, and the phantom is moved to align the cylinder axis of the phantom with the center of the scan based on information regarding the calculated displacement.

According to the third embodiment of the invention, there is no need to perform a manual operation to align the cylinder axis of the phantom with the center of the scan. Thus, it becomes possible to quickly and easily align the phantom, regardless of the level of skill of the operator.

According to the fourth embodiment of the invention, when aligning a phantom that is set on a top plate of a bed, tomographic image data is generated on the phantom based on the results of detecting X-rays by an X-ray detector, the angle of gradient of the cylinder axis of the phantom is calculated relative to the normal direction (slice direction) of the rotation plane of rotation of the X-ray generator and the X-ray detector by a rotation drive unit, based on the generated tomographic image data, and information for alignment of the phantom is displayed by the display device, based on the calculated angle of gradient.

According to the fourth embodiment of the invention, the operators can easily obtain information for alignment, based on the gradient of the phantom relative to the slice direction. Thus, it becomes possible to quickly and easily correct the gradient of the phantom, regardless of the level of skill of the operator.

According to the fifth embodiment of the invention, when aligning a phantom that is set on a top plate of a bed, tomographic image data is generated on the phantom, based on the results of detecting X-rays by an X-ray detector, the angle of gradient of the cylinder axis of the phantom is calculated relative to the normal direction (slice direction) of the rotation plane of rotation of the X-ray generator and the X-ray detector by a rotation drive unit, based on the generated tomographic image data, and the X-ray generator and X-ray detector are inclined integrally to align the slice direction to the cylinder axis of the phantom, based on the calculated angle of gradient.

According to the fifth embodiment of the invention, there is no need to perform a manual operation to correct the gradient of the phantom. Thus, it becomes possible to quickly and easily align the phantom, regardless of the level of skill of the operator.

According to the sixth embodiment of the invention, when aligning a phantom that is set on a top plate of a bed, the angle of gradient of the cylinder axis of the phantom is calculated relative to the normal direction (slice direction) of the rotation plane of rotation by a rotation drive unit, based on the results of detecting X-rays by an X-ray detector, and the phantom is inclined to align the cylinder axis of the phantom with the slice direction, based on the calculated angle of gradient.

According to the sixth embodiment of the invention, there is no need to perform a manual operation to correct the gradient of the phantom. Thus, it becomes possible to quickly and easily align the phantom, regardless of the level of skill of the operator.

According to the seventh embodiment of the invention, when aligning a phantom that is set on a top plate of a bed, tomographic image data is generated on the phantom, based on the results of detecting X-rays by an X-ray detector, a partial tomographic image data corresponding to the housing of the phantom is extracted from the generated tomographic image data, coordinates of the center of a circle passing through more than two different points in the extracted partial tomographic image data are calculated, displacement of the cylinder axis of the phantom relative to the center of the scan is calculated, based on the calculated coordinates of the center of the circle and the coordinates of the center of rotation (center of the scan) of the X-ray generator and the X-ray detector that are stored in advance by a storage device, and the error relative to the circle of multiple different points in the extracted partial tomographic image data is calculated, whether the calculated error exceeds the predetermined value is determined, and when the error is determined to not exceed the predetermined value, displacement of the cylinder axis of the phantom relative to the above calculated center of the scan is displayed.

Furthermore, according to the seventh embodiment, when the error is determined to exceed the predetermined value, coordinates of the center of an ellipse passing through more than two different points in the above extracted partial tomographic image data are calculated, displacement of the cylinder axis of the phantom relative to the center of the scan is calculated, based on the calculated coordinates of the center of an ellipse and the above stored coordinates of the center of the scan, and a horizontal radius and a vertical radius of the ellipse are each calculated, the angle of gradient of the cylinder axis of the phantom relative to the above normal direction (slice direction) of the rotation plane of rotation is calculated, based on the calculated radiuses of horizontal direction and vertical direction, and the calculated displacement and angle of gradient of the cylinder axis of the phantom are displayed by a display device.

According to the seventh embodiment of the invention, when the abovementioned error is determined to not exceed the predetermined value, or in other words, when the angle of gradient of the phantom relative to the slice direction is small, displacement of the cylinder axis of the phantom relative to the center of the scan that was precisely obtained by the process described in the former clause is displayed, and when the angle of gradient of the phantom is large, the process described in the latter clause is performed to calculate and display the angle of gradient of the phantom and displacement of the cylinder axis. Therefore, in either case, the operators can ascertain the position of the phantom with high precision, and it becomes possible to quickly and easily align the phantom, regardless of the level of skill of the operator.

According to the eighth embodiment of the invention, when aligning a phantom that is set on a top plate of a bed, tomographic image data is generated on the phantom, based on the results of detecting X-rays by an X-ray detector, a partial tomographic image data corresponding to the housing of the phantom is extracted from the generated tomographic image data, coordinates of the center of a circle passing through more than two different points in the extracted partial tomographic image data are calculated, displacement of the cylinder axis of the phantom relative to the center of the scan is calculated, based on the calculated coordinates of the center of the circle and the coordinates of the center of rotation (center of the scan) of the X-ray generator and the X-ray detector that are stored in advance by a storage device, and the error relative to the circle of multiple different points in the extracted partial tomographic image data is calculated, whether the calculated error exceeds the predetermined value is determined, and when the error is determined to not exceed the predetermined value, the top plate is moved to align the cylinder axis of the phantom with the center of the scan, based on displacement of the cylinder axis of the phantom relative to the above calculated center of the scan.

Furthermore, according to the eighth embodiment, when the error is determined to exceed the predetermined value, coordinates of the center of an ellipse passing through more than two different points in the above extracted partial tomographic image data are calculated, displacement of the cylinder axis of the phantom relative to the center of the scan is calculated, based on the calculated coordinates of the center of an ellipse and the above stored coordinates of the center of the scan, and a horizontal radius and vertical radius of the ellipse are each calculated, the angle of gradient of the cylinder axis of the phantom relative to the above normal direction (slice direction) of the rotation plane of rotation is calculated, based on the calculated radiuses of horizontal direction and vertical direction, the X-ray generator and the X-ray detector are inclined integrally to align the slice direction to the cylinder axis of the phantom, based on the calculated angle of gradient, and the top plate is moved to align the cylinder axis of the phantom with the center of the scan, based on displacement of the cylinder axis of the phantom relative to the above calculated center of the scan.

According to the eighth embodiment of the invention, when the above error is determined to not exceed the predetermined value, or in other words, when the angle of gradient of the phantom relative to the slice direction is small, cylinder axis of the phantom relative to the center of the scan can be precisely and automatically aligned through the process described in the former clause, and when the angle of gradient of the phantom is large, the cylinder axis of the phantom relative to the center of the scan and correction of the angle of gradient can be precisely and automatically aligned through the process described in the latter clause. Therefore, it becomes possible to quickly and easily align the phantom, regardless of the level of skill of the operator.

The ninth embodiment of the invention is a phantom retaining tool for retaining the phantom with a cylindrical housing filled with filling on a top plate of a bed in the X-ray CT apparatus, and it is controlled by the control device of the X-ray CT apparatus, and comprises a phantom retaining tool for vertically and/or horizontally moving the phantom that is retained on the top plate of the bed.

According to the ninth embodiment of the invention, the phantom can be aligned with high precision compared to the case of moving the top plate. Moreover, since the alignment of the phantom is conducted by the control of the control device, it is possible to simplify the operation of alignment.

The tenth embodiment of the invention comprises a phantom retaining tool for retaining the phantom with a cylindrical housing filled with filling on a top plate of a bed apparatus of X-ray CT apparatus, which collects data while rotating the X-ray generator for generating X-rays and the X-ray detector for the generated X-rays, and generating tomographic image data, based on the collected data, and a phantom retaining tool for tilting the phantom, which is retained on the top plate, in the direction of the gradient relative to the normal direction of the rotation plane of the X-ray generator and the X-ray detector as a baseline controlled by the control device of the X-ray CT apparatus.

According to the tenth embodiment of the invention, the phantom can be aligned with high precision compared to the case of tilting the X-ray generator and X-ray detector (gantry). Moreover, because the phantom is aligned through control by the control device, it is possible to simplify the operation of alignment.

DETAILED DESCRIPTION OF THE INVENTION

An example of embodiments of the X-ray CT apparatus, a method for aligning the phantom, and a phantom retaining tool related to the invention will be described in detail with relevant reference to figures.

Instances from each of the first to third embodiments of the X-ray CT apparatus related to the invention are described below. The first embodiment describes X-ray CT apparatus with a composition in which the setting of the phantom is calculated and the calculated result is displayed. Furthermore, the second embodiment describes X-ray CT apparatus with a composition in which the setting of the phantom is calculated and the setting of the phantom is automatically corrected by controlling a bed and/or a gantry, based on the calculated result. Moreover, the third embodiment describes X-ray CT apparatus and a phantom retaining tool with a composition in which the setting of the phantom is calculated, and the phantom is moved, based on the calculated result. Then, it describes a computer program for running this type of alignment method of the phantom on X-ray CT apparatus.

First Embodiment

Overall Composition of Apparatus

Figure 2:
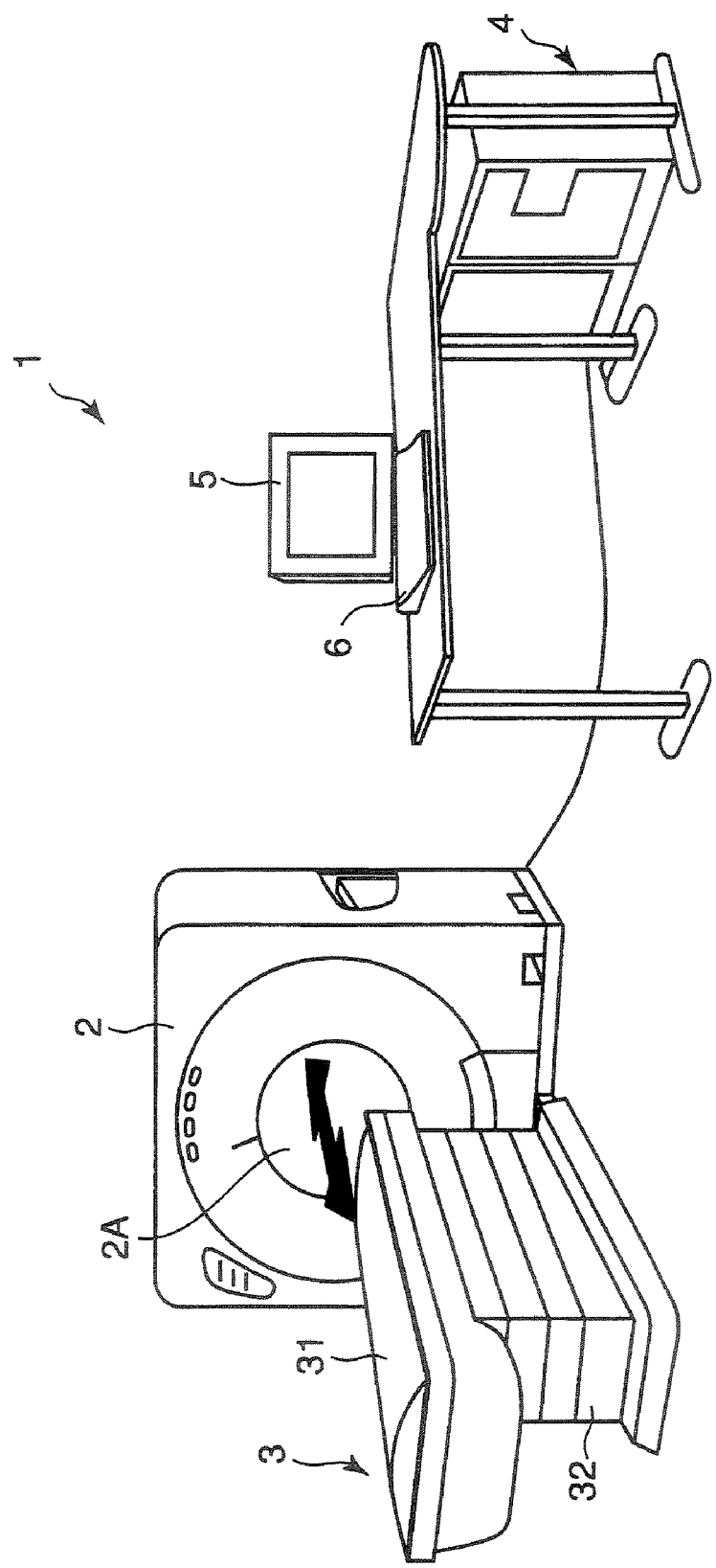
FIG. 2 is a schematic perspective view showing an example the appearance of the composition of the first embodiment of X-ray CT apparatus related to the invention.
Figure 3:
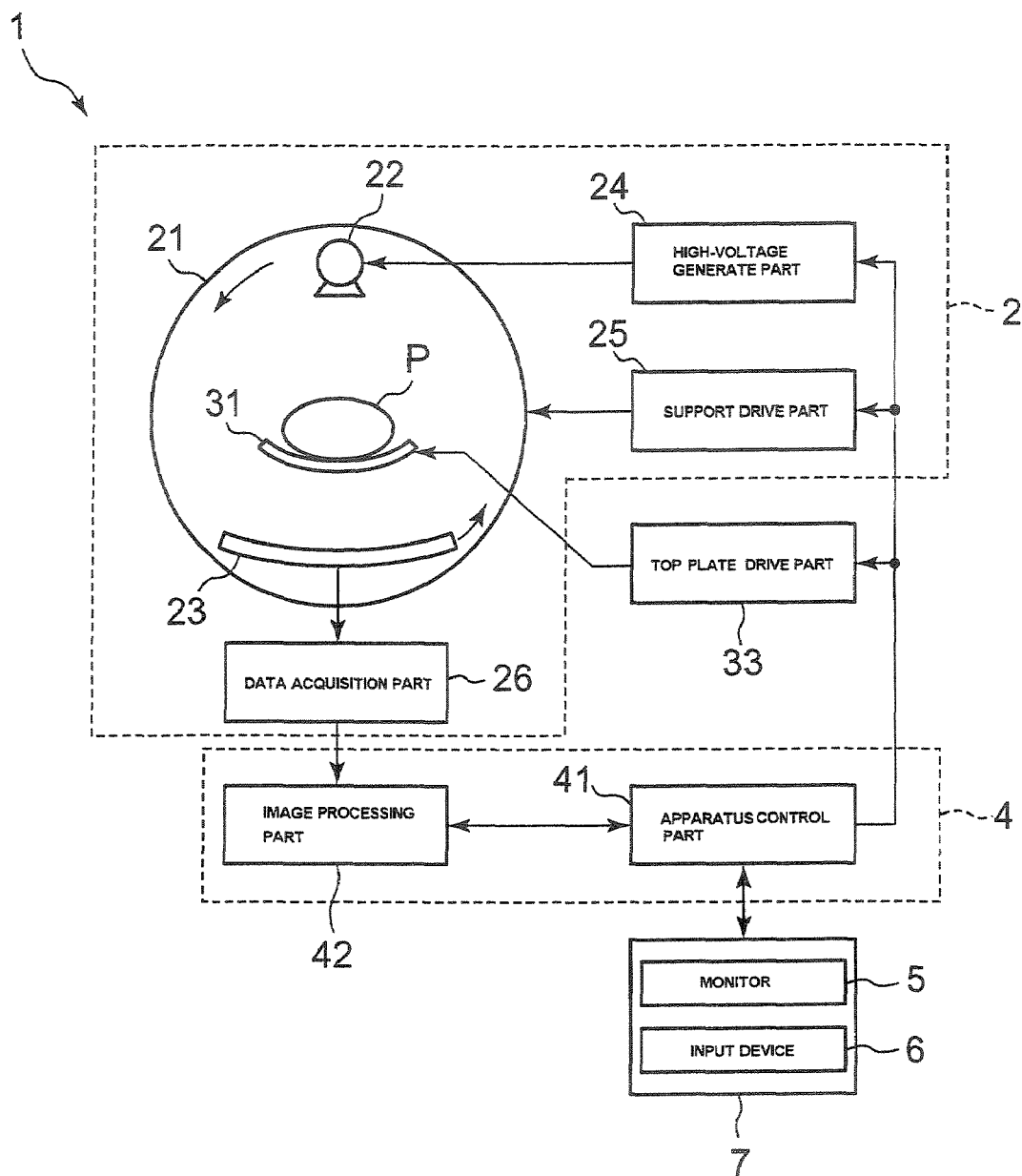
FIG. 3 is a schematic block diagram showing an example of the internal composition of the first embodiment of X-ray CT apparatus related to the invention.

The overall composition of X-ray CT apparatus related to the first embodiment of the invention will be described with reference to FIG. 2 and FIG. 3. FIG. 2 shows the appearance of the composition of the X-ray CT apparatus 1 related to the embodiment. Moreover, FIG. 3 shows an internal composition of the X-ray CT apparatus 1. The X-ray CT apparatus 1 related to the embodiment is as is conventionally comprised, including a gantry 2, bed 3, computer apparatus 4, monitor 5, and input device 6.

The monitor 5 and input device 6 are used as the console 7 of the X-ray CT apparatus 1 (refer to FIG. 3). The monitor 5 relates to an example of the "display device" of the invention, and consists of arbitrary display apparatus such as an LCD (liquid crystal display) or a CRT (cathode ray tube). The input device 6 consists of arbitrary input apparatus such as a keyboard, mouse, track ball, control panel, or a touch panel.

The gantry 2 has a built-in rotational support 21 as shown in FIG. 3. This support 21 supports an X-ray tube 22 that relates to an example of the "X-ray generator" of the invention and an X-ray detector 23 that relates to an example of the "X-ray detector" of the invention. The X-ray tube 22 generates X-rays based on predetermined tube voltage and tube current provided by a high-voltage generate part 24, and it irradiates a fan beam or cone beam of the X-rays toward the object P situated inside the opening 2A of the gantry 2. The X-ray detector 23 is supported in a position opposite to the X-ray tube 22, and it has a composition in which multiple X-rays detecting elements that detect the radiation dose of X-rays transmitted through the object P are arranged in an array.

The support 21 is rotated around the opening 2A by a support drive part 25. The X-ray tube 22 and the X-ray detector 23 are rotated with rotation of the support 21 to scan an object P with X-rays, and detect dose data of X-rays transmitted through the object P from various directions. The transmitted X-ray dose data (detection signal) detected by the X-ray detector 23 is sent to the data acquisition part 26. The data acquisition part 26 is a so-called DAS (data acquisition system), and has data collection elements arranged in an array as each of the X-rays detecting elements of the X-ray detector 23, and collects the transmitted X-ray dose data (detection signal) detected by the X-ray detector 23. The data acquisition part 26 applies an amplification process and A/D (analog/digital) conversion process to the collected data and transmits it to computer apparatus 4.

The support drive part 25 is caused to not only rotate the support 21 as described above but also tilt the support 21 relative to the object P. The support drive part 25 relates to an example of the "rotation drive unit" and "gradient drive unit" of the invention. In addition, it is possible to separately set the rotation drive unit and gradient drive unit.

The bed 3 comprises a top plate 31 on which an object P is placed and a bed base 32 that supports the top plate 31, as shown in FIG. 2. On the bed base 32, a top plate drive part 33 is set to move the top plate 31 toward the front and behind direction (direction of the arrow in FIG. 2; horizontal direction), right and left direction (horizontal direction perpendicular to the front and behind direction), up and down direction (vertical direction) (refer to FIG. 3). In addition, the above front and behind direction is the direction of the body axis of an object P on the top plate 31.

The computer apparatus 4 consists, for example, of a general computer equipped with a microprocessor, memory, mass-storage system, and an interface. The microprocessor includes a CPU (central processing unit) and/or MPU (micro processing unit) etc. The memory includes RAM (random access memory) and/or ROM (read-only memory) etc. The mass-storage system includes a hard disk drive etc. The interface is for sending and receiving data and signals between other apparatus (such as a gantry 2, bed 3, consol 7, and other computer apparatus in the network (not shown in the figure)).

The computer apparatus 4 has an apparatus control part 41 for controlling the action of each part of the X-ray CT apparatus 1, and an image processing part 42 is set to perform a generation process of image data and various image processes, based on data collected by the gantry 2. The apparatus control part 41 controls the rotating motion and tilting motion of the support 21 by the support drive part 24, control of the motion of the X-ray tube 22 by the high-voltage generate part 24, control of the motion of the X-ray detector 23, control of the action of the data acquisition part 26, and control of the motion of the top plate 31 by the top plate drive part 33. The composition and action of the image processing part 42 will be explained in detail below.

Composition of Control System

Figure 4:
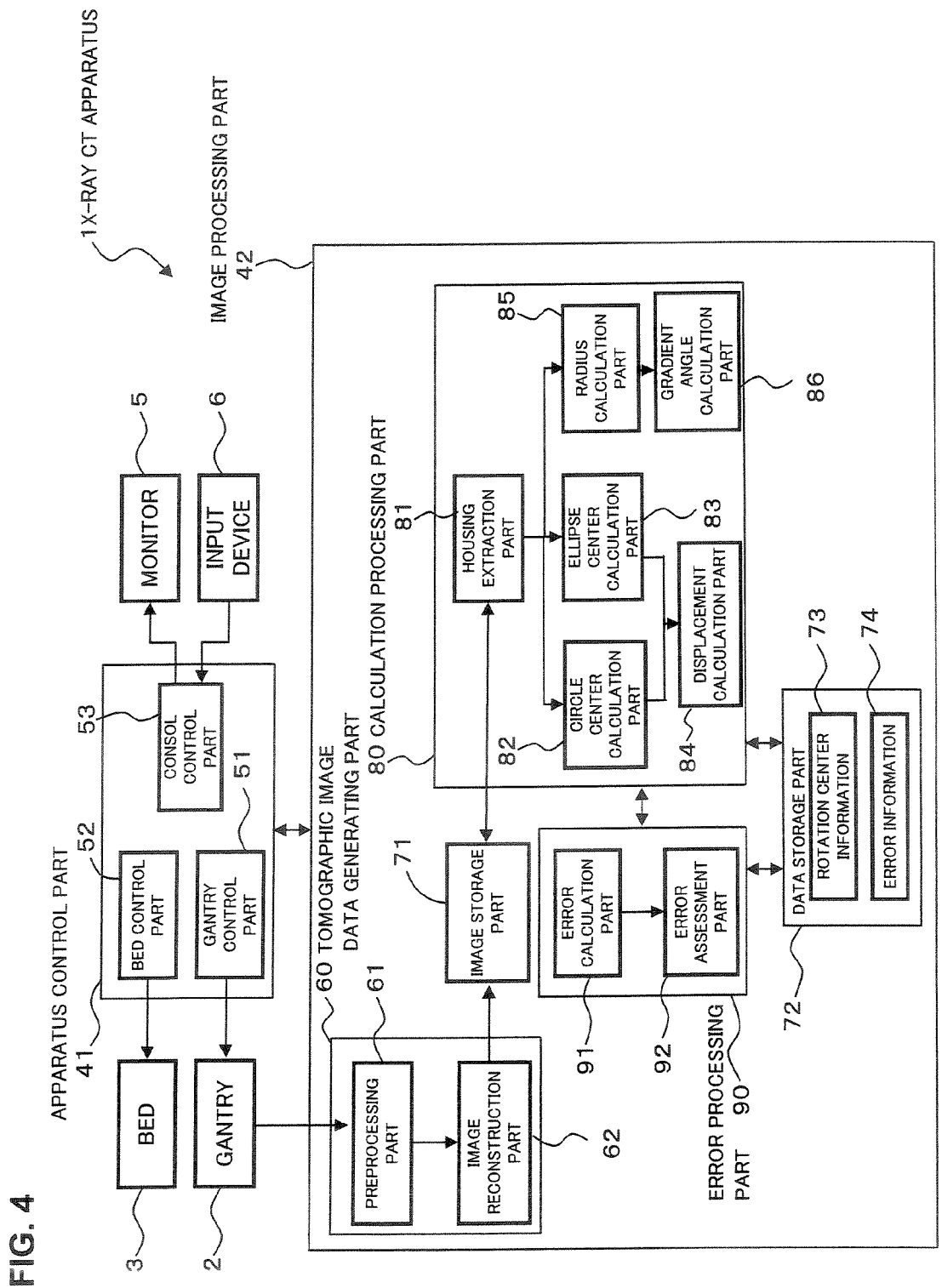
FIG. 4 is a schematic block diagram showing an example of the composition of the control system of the first embodiment of X-ray CT apparatus related to the invention.

FIG. 4 shows the internal composition of the X-ray CT apparatus 1 related to the embodiment. Composition of control system of the X-ray CT apparatus 1, especially composition of the computer apparatus 4, will be described in detail below with reference to FIG. 4. In addition, to avoid making the figure complicated, a drawing of the block indicating the computer apparatus 4 was omitted in FIG. 4.

Apparatus Control Part

The apparatus control part 41 of the computer apparatus 4 includes a microprocessor built into the computer apparatus 4. This microprocessor performs the following control processes by loading the computer programs, which are stored in storage devices such as ROM and hard disk drive that is built into the computer apparatus 4, on RAM.

Installed in the apparatus control part 41 are a gantry control part 51 that controls the gantry 2, a bed control part 52 that controls the bed 3, and a consol control part 53 that controls the monitor 5 and input device 6 (consol 7).

Gantry Control Part

The gantry control part 51 is responsible for controlling each part of the gantry 2. For example, the gantry control part 51 sends control signals to the support drive part 25 to control the rotating motion and tilting action of the support 21. In addition, the gantry control part 51 sends control signals to the high-voltage generate part 24 to control the action of the X-ray tube 22 to generate X-rays. Moreover, the gantry control part 51 controls the action of the X-ray detector 23 and controls the action of the data acquisition part 26.

Bed Control Part

The bed control part 52 sends control signals to the top plate drive part 33 of the bed 3 and moves the top plate 31 to the front and behind, right and left, and up and down directions.

Consol Control Part

The consol control part 53 sends image signals (e.g., RGB video signals for color images) to the monitor 5 to display the target image on the monitor 5.

Moreover, the consol control part 53 receives input of the operation signal from the input device 6, and performs the action requested by the operation signal. For example, when an operation to tilt the gantry 2 is performed, an operation signal corresponding to the tilting request operation is input into the consol control part 53 from the input device 6. The consol control part 53 sends the operation signal to the gantry control part 51. The gantry control part 51 tilts the gantry 2 by the requested angle, based on the operation signal. Furthermore, when an operation to move the top plate 31 of the bed 3 is performed, an operation signal corresponding to the top plate movement request operation is input into the consol control part 53 from the input device 6. The consol control part 53 sends the operation signal to the bed control part 52. The bed control part 52 moves the top plate 31, based on the operation signal.

Image Processing Part

The image processing part 42 of the computer apparatus 4 includes a microprocessor such as CPU, as the apparatus control part 41. This microprocessor performs the following control processes by loading computer programs, which are stored in storage devices that are embedded in the computer apparatus 4. Moreover, the image processing part 42 includes storage devices for storing various data involving processes and image data (tomographic image data) of the reconstructed image.

In addition, when the computer apparatus 4 is connected to a network such as a LAN (local area network), computer programs can be stored on a server on the network. The computer apparatus 4 obtains the computer programs via the network. In other words, the computer apparatus 4 and the server can be configured as a client-server system.

Furthermore, installed in the image processing part 42 are a tomographic image data generation part 60, image storage part 71, data storage part 72, calculation process part 80, and an error processing part 90. Each of these will be described below.

Tomographic Image Data Generation Part

The tomographic image data generation part 60 relates to an example of the "tomographic image data generator" of the invention. The tomographic image data generation part 60 includes a preprocessing part 61 and an image reconstruction part 62, having—for example—a microprocessor such as a CPU mounted on a circuit board (also referred to as a reconstruction board) as in conventional X-ray CT apparatus.

The preprocessing part 61 generates the projection data served for image reconstruction. More specifically, the preprocessing part 61 performs a series of processes called preprocessing, such as logarithmic calculation of data, reference correction, water calibration, beam hardening correction, and motion correction of data sent from the data acquisition part 26 of the gantry 2.

The image reconstruction part 62 performs a process using an image reconstruction method on the projection data generated by the preprocessing part 61 and generates tomographic image data of the object P. In addition, as for the image reconstruction method used, there are publicly known methods such as the convolution backprojection method, the fan-beam convolution backprojection method (divergent ray convolution backprojection method), and the two-dimensional Fourier transformation method).

Image Storage Part

The image storage part 71 stores the tomographic image data generated by the tomographic image data generation part 60. The image storage part 71 includes a mass-storage system such as a hard disk drive.

Data Storage Part

The data storage part 72 stores various data used in the process performed by the image processing part 42. The data storage part 72 includes a non-volatile storage unit such as ROM and a hard disk drive. In the data storage part 72, specially, rotation center information 73 and error information 74 are stored in advance. This data storage part 72 relates to an example of a "storage device" of the invention.

The rotation center information 73 shows coordinates of the center of the scan of X-rays by the gantry 2, or in other words, coordinates of the center of rotation of the X-ray tube 22 and the X-ray detector 23 by the support drive part 25. For example, when the display region of a reconstructed image of the monitor 5 is 512×512 pixels, this rotation center information 73 includes coordinates (255, 255) as the coordinates of the center of the scan. This coordinates of the center of the scan are set in advance. In addition, a reconstructed image is displayed in the monitor 5 so as to place the center O of the scan in the center position of the display region (refer to FIG. 5A, FIG. 5B, FIG. 6, and FIG. 7).

The error information 74 is referred in the process by the error processing part 90, and shows a threshold value of error that becomes the base of assessment by the error assessment part 92 described below. The error information 74 will be described in detail in the description of the error processing part 90.

In addition, when the abovementioned client-server system is employed, it can be configured so that the storage content of the data storage part 72 is stored on the server and read-out via the network to be referenced accordingly.

Calculation Process Part

Figure 1A:
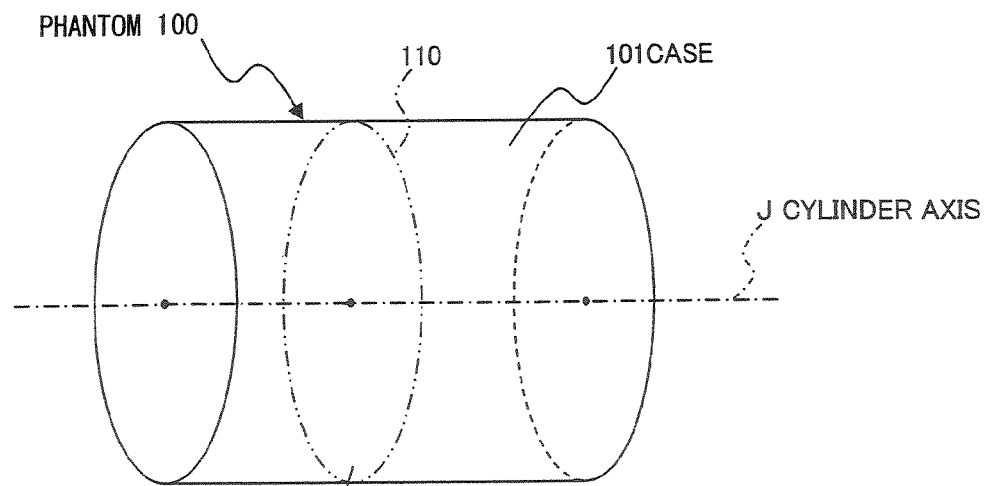
FIG. 1A is a schematic perspective view showing the appearance of the composition of a cylindrical phantom to evaluate the performance of X-ray CT apparatus.
Figure 1B:
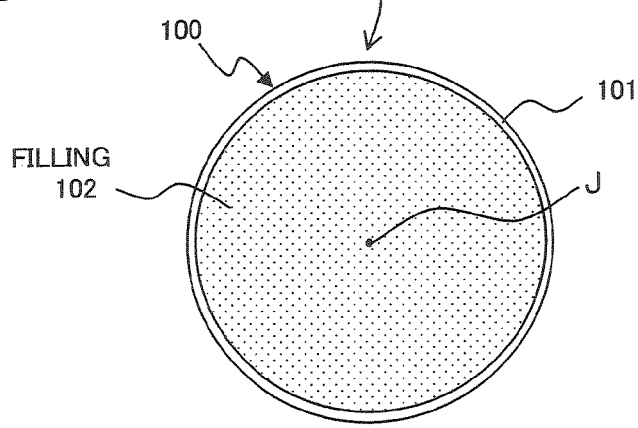
FIG. 1B is a schematic cross-section diagram showing the shape of a cross-section of a cylindrical phantom for performance evaluation of X-ray CT apparatus.

The calculation process part 80 relates to an example of the "calculation unit" of the invention. The calculation process part 80 includes a microprocessor such as CPU that runs computer programs for evaluating performance of X-ray CT apparatus 1. For evaluating the performance of the X-ray CT apparatus 1, the previously described phantom 100 (refer to FIG. 1A, FIG. 1B) is used. The phantom 100 is mounted on a top plate 31 of a bed 3 with the position of the cylinder axis J adjusted to align with the slice direction using the prescribed mounting tool (phantom retaining tool).

The calculation process part 80 comprises a housing extraction part 81, a circle center calculation part 82, an ellipse center calculation part 83, a displacement calculation part 84, a radius calculation part 85, and a gradient angle calculation part 86.

Housing Calculation Part

The housing extraction part 81 relates to an example of the "extraction unit" of the invention. The housing extraction part 81 analyzes image data (tomographic image data) of the reconstructed image of the phantom 100 generated by the tomographic image data generation part 60. Then it extracts tomographic image data (partial tomographic image data) of the part that corresponds to the case 101 (housing) of the phantom 100. The housing extraction part 81, for example, extracts the part that corresponds to the case 101 by analyzing the CT number of each pixel in tomographic image data of the phantom 100.

Figure 5A:
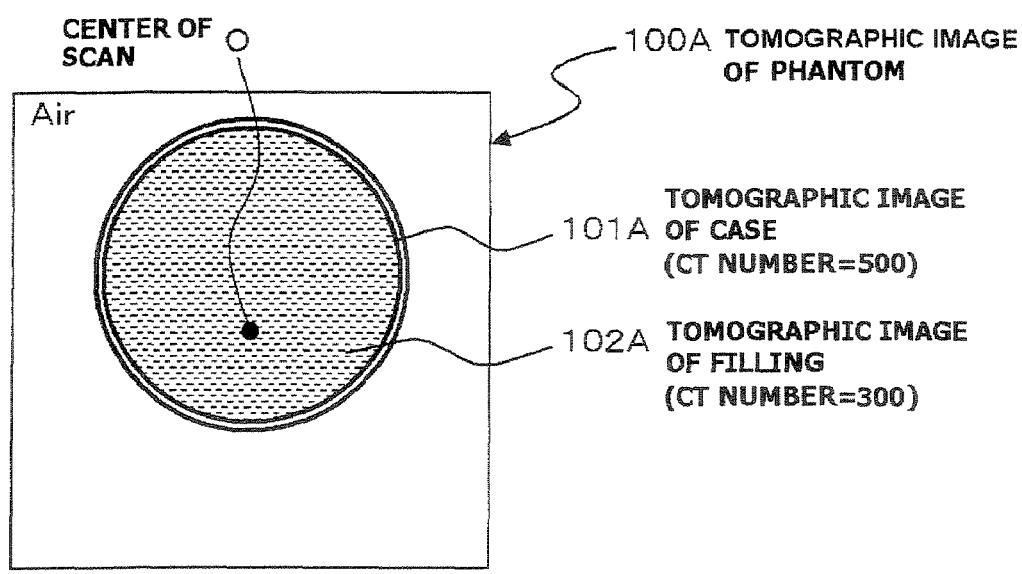
FIG. 5A shows an outline of a tomographic image, based on tomographic image data of the phantom generated by the tomographic image generation part of the first embodiment of X-ray CT apparatus related to the invention.
Figure 5B:
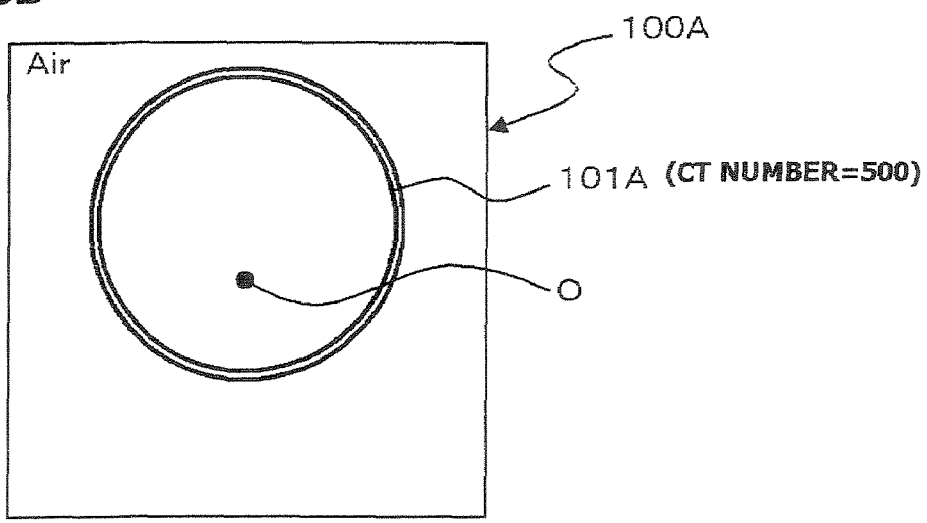
FIG. 5B shows an outline of a tomographic image, based on the partial tomographic image data corresponding to the case of the phantom extracted by the case extraction part in the first embodiment of X-ray CT apparatus related to the invention.

FIG. 5A and FIG. 5B show an example of the tomographic image data extraction process by the housing extraction part 81. In addition, in FIG. 5A, FIG. 5B, and FIG. 6 described below, a tomographic image of the phantom 100 is shown in a circular form with the assumption that the phantom 100 is placed along the slice direction (Z direction). In addition, positioning of a phantom 100 on a gradient relative to the slice direction will be described later with reference to FIG. 7.

The image (tomographic image 100A), based on tomographic image data of the phantom 100, as shown in FIG. 5A, includes a tomographic image 101A, which is the part that corresponds to the case 101 of the phantom 100, and a tomographic image 102A, which is the part that corresponds to the filling 102 within the case 101. In addition, the background region of the tomographic image 101A of the case 101 corresponds to air around the phantom 100 placed on the top plate 31.

The phantom 100 (especially the case 101) is formed from a known material. It is possible to obtain the CT number of the part that corresponds to the case 101 in the tomographic image data on the phantom 100 in advance by preliminary measurement, for example. Moreover, it is also possible to similarly obtain the CT number of the part that corresponds to the filling 102 in advance. Here, the CT number of the tomographic image 101A that corresponds to the case 101, or in other words, the CT number of partial tomographic image data that corresponds to the case 101 from among the tomographic image data is set to 500. Furthermore, the CT number of the tomographic image 102A that corresponds to the filling 102 is set to 300. These CT numbers are stored in advance in a data storage part 72, for example. In addition, there is no need to store the CT number of the tomographic image 102A of the filling 102.

The housing extraction part 81 extracts pixels having a CT number (=500) that corresponds to the case 101 by referring to the CT number of each pixel of the tomographic image data of the tomographic image such as in FIG. 5A. This causes the tomographic image (partial tomographic image data) of the part that corresponds to the case 101 to be extracted from the tomographic image 100A (tomographic image data) of the phantom 100, as shown in FIG. 5B.

In addition, when displaying the processing results of the housing extraction part 81 on the monitor 5, the CT number of pixels other than the pixels that correspond to the partial tomographic image data are set to 0 and are subsequently displayed. At that time, for example, the CT number of pixels from among the partial tomographic image data other than the part that corresponds to the outer circumference surface of the case 101 can also be set to 0. This causes the tomographic image of the part that corresponds to the case 101 (its outer circumference surface) to be displayed on a black background.

Circle Center Calculation Part

The circle center calculation part 82 relates to an example of the "circle center calculation unit" of the invention, and it calculates the coordinates of the center of the circle passing through three different points in a partial tomographic image data extracted by the housing extraction part 81.

Figure 6:
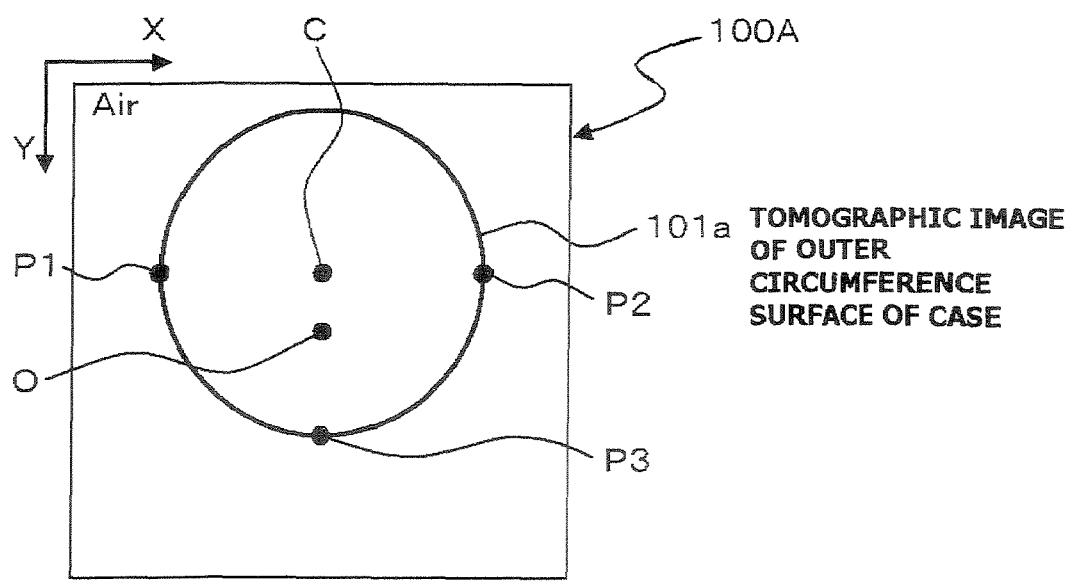
FIG. 6 is a schematic diagram for describing an example of selection modes for three different points on the partial tomographic image data by a circle center calculation part of the first embodiment of X-ray CT apparatus related to the invention.

The three points used in a calculation of coordinates of the center of the circle are selected, for example, from the part corresponding to the outer circumference surface of the case 101. In addition, the three points may be selected, for example, from the part that corresponds to the inner circumference surface of the case 101. An example of selection mode for the three points is shown in FIG. 6. In FIG. 6, the point P1 ($x_1$, $y_1$) with the smallest X coordinate, the point P2 ($x_2$, $y_2$) with the largest X coordinate, and the point P3 ($x_3$, $y_3$) with the largest Y coordinate are selected on the tomographic image 101A of the outer circumference surface of the case 101. In addition, the X coordinates are the coordinates of the horizontal direction perpendicular to the slice direction (Z direction), and the Y coordinate is a coordinate of the vertical direction.

The search process of the point P1 can be performed, for example, by searching the coordinates of the pixel with the smallest X coordinate from among the pixels with a CT number=500 (CT number responding to the case 101). A search for the point P2 can be performed by searching the coordinates of the pixel with the largest X coordinates from among the pixels with a CT number=500. A search for the point P3 can be performed by searching the coordinates of the pixel with the largest Y coordinate from among the pixels with a CT number=500.

Here, fore example, when there are multiple pixels with the largest Y coordinate from among the pixels with a CT number=500, because it is assumed that the phantom 100 is placed in a position that largely shifts toward the +Y direction, it can be switched so as to search for the pixel with the smallest Y coordinates as the CT number=500. Moreover, when there are multiple pixels with the smallest (the largest) X coordinate, because it is assumed that the phantom 100 largely shifts toward the X direction, it can be switched so as to search the pixel with the smallest (largest) X direction, the pixel with the largest and the pixel with the smallest Y coordinate.

Now, for the three points—P1, P2 and P3—selected from the tomographic image 101A of the case 101 (in other words, selected from the partial tomographic image data) to exist on the same circumference, the following condition must be met.

$$\begin{vmatrix} x^2+y^2 & x & y & 1 \\ x_1^2+y_1^2 & x_1 & y_1 & 1 \\ x_2^2+y_2^2 & x_2 & y_2 & 1 \\ x_3^2+y_3^2 & x_3 & y_3 & 1 \end{vmatrix} = 0 \qquad \text{Equation 1}$$

Moreover, if this equation of the circle is expressed as in the following Equation 2, the coordinates $(x_0, y_0)$ of the center C and the radius r are expressed as in Equation 3. Further, the coefficients a, d, e, and f of Equation 2, which are used in Equation 3, are given by the equations in Equation 4.

$$ax^2 + cy^2 + dx + ey + f = 0 \qquad \text{Equation 2}$$

$$x_0 = -\frac{d}{2a}$$
$$y_0 = -\frac{e}{2a} \qquad \text{Equation 3}$$
$$r = \sqrt{\left(\frac{d^2+e^2}{4a^2} - \frac{f}{a}\right)}$$

$$a = \begin{vmatrix} x_1 & y_1 & 1 \\ x_2 & y_2 & 1 \\ x_3 & y_3 & 1 \end{vmatrix} \qquad \text{Equation 4}$$

$$d = \begin{vmatrix} x_1^2+y_1^2 & y_1 & 1 \\ x_2^2+y_2^2 & y_2 & 1 \\ x_3^2+y_3^2 & y_3 & 1 \end{vmatrix}$$

$$e = \begin{vmatrix} x_1^2+y_1^2 & x_1 & 1 \\ x_2^2+y_2^2 & x_2 & 1 \\ x_3^2+y_3^2 & x_3 & 1 \end{vmatrix}$$

$$f = \begin{vmatrix} x_1^2+y_1^2 & x_1 & y_1 \\ x_2^2+y_2^2 & x_2 & y_2 \\ x_3^2+y_3^2 & x_3 & y_3 \end{vmatrix}$$

The circle center calculation part 82 selects the three points—P1 $(x_1, y_1)$, P2 $(x_2, y_2)$, and P3 $(x_3, y_3)$—from the partial tomographic image data extracted by the housing extraction part 81. Then, the circle center calculation part 82 calculates each value of the coefficients—a, d, e, and f—of Equation 2 by applying the coordinate values of these three points—P1 $(x_1, y_1)$, P2 $(x_2, y_2)$, and P3 $(x_3, y_3)$—to each equation in Equation 4, and it calculates the coordinates of the center C $(x_0, y_0)$ by substituting the coefficient values to the first and second equations of Equation 3.

Ellipse Center Calculation Part

The ellipse center calculation part 83 relates to an example of the "ellipse center calculation unit" of the invention. The ellipse center calculation part 83, as described later in the section on "action," acts when a phantom 100 is positioned on a gradient relative to the slice direction (Z direction), and calculates the coordinates of the center of the ellipse passing through the four different points in the partial tomographic image data extracted by the housing extraction part 81. Here, the center of the ellipse means the middle point of two focal points of the ellipse, which is the intersection point of the long axis and the short axis of the ellipse.

Figure 7:
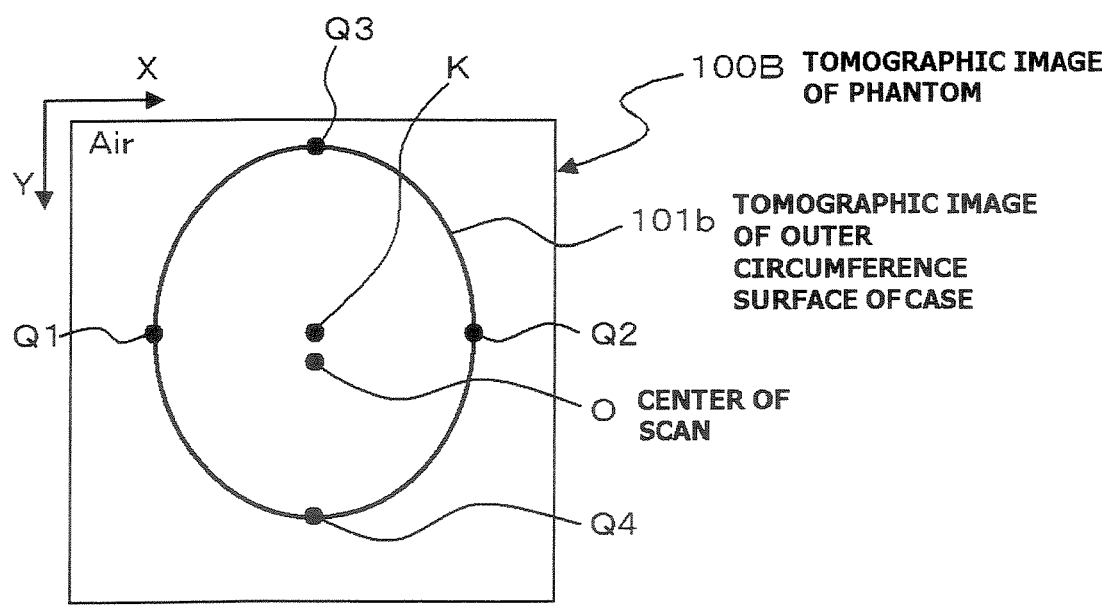
FIG. 7 is a schematic diagram for describing an example of selection modes for four different points on the partial tomographic image data by an ellipse center calculation part of the first embodiment of X-ray CT apparatus related to the invention.

When a phantom 100 is positioned on a gradient relative to the slice direction, the tomographic image of the part that corresponds to the case 101 (partial tomographic image data) forms an elliptical shape (refer to the tomographic image 101b in FIG. 7). In addition, determination of whether a phantom 100 is inclined is performed by the error processing part 90 explained later.

The four points used for the ellipse center coordinate calculation, for example, are selected from the part that corresponds to the outer circumference surface of the case 101. These four points may be the part corresponding to the inner circumference surface of the case 101. An example of the mode of selecting the four points is shown in FIG. 7. FIG. 7 shows an elliptical-shape tomographic image 101b of the outer circumference surface of the case 101 in a tomographic image 100B of the phantom 100, which is positioned in a vertical (Y direction) gradient relative to the slice direction (Z direction). In this embodiment, the point Q1 $(\xi_1, \eta_1)$ with the smallest X coordinate, the point Q2 $(\xi_2, \eta_2)$ with the largest X coordinate, the point Q3 $(\xi_3, \eta_3)$ with the smallest Y coordinate, and the point Q4 $(\xi_4, \eta_4)$ with the largest Y coordinate in the tomographic image 101b of the outer circumference surface are selected as the four points.

For these four points—Q1, Q2, Q3 and Q4—to exist on the same ellipse, the following condition must be met.

$$\begin{vmatrix} x^2 & y^2 & x & y & 1 \\ \xi_1^2 & \eta_1^2 & \xi_1 & \eta_1 & 1 \\ \xi_2^2 & \eta_2^2 & \xi_2 & \eta_2 & 1 \\ \xi_3^2 & \eta_3^2 & \xi_3 & \eta_3 & 1 \\ \xi_4^2 & \eta_4^2 & \xi_4 & \eta_4 & 1 \end{vmatrix} = 0 \qquad \text{Equation 5}$$

Moreover, when this equation of the ellipse is expressed as in the following Equation 6, the coefficients of the equation are given by the equations in Equation 7. Furthermore, the coordinates of the ellipse center K $(\xi_0, \eta_0)$, the radius $r_x$ of the X direction, and the radius $r_y$ of the Y direction are each expressed as in Equation 8.

$$Ax^2 + Cy^2 + Dx + Ey + F = 0 \qquad \text{Equation 6}$$

$$A = \begin{vmatrix} \eta_1^2 & \xi_1 & \eta_1 & 1 \\ \eta_2^2 & \xi_2 & \eta_2 & 1 \\ \eta_3^2 & \xi_3 & \eta_3 & 1 \\ \eta_4^2 & \xi^4 & \eta_4 & 1 \end{vmatrix} \qquad \text{Equation 7}$$

$$C = \begin{vmatrix} \xi_1^2 & \xi_1 & \eta_1 & 1 \\ \xi_2^2 & \xi_2 & \eta_2 & 1 \\ \xi_3^2 & \xi_3 & \eta_3 & 1 \\ \xi_4^2 & \xi^4 & \eta_4 & 1 \end{vmatrix}$$

$$D = \begin{vmatrix} \xi_1^2 & \eta_1^2 & \eta_1 & 1 \\ \xi_2^2 & \eta_2^2 & \eta_2 & 1 \\ \xi_3^2 & \eta_3^2 & \eta_3 & 1 \\ \xi_4^2 & \eta_4^2 & \eta_4 & 1 \end{vmatrix}$$

$$E = \begin{vmatrix} \xi_1^2 & \eta_1^2 & \xi_1 & 1 \\ \xi_2^2 & \eta_2^2 & \xi_2 & 1 \\ \xi_3^2 & \eta_3^2 & \xi_3 & 1 \\ \xi_4^2 & \eta_4^2 & \xi_4 & 1 \end{vmatrix}$$

$$F = \begin{vmatrix} \xi_1^2 & \eta_1^2 & \xi_1 & \eta_1 \\ \xi_2^2 & \eta_2^2 & \xi_2 & \eta_2 \\ \xi_3^2 & \eta_3^2 & \xi_3 & \eta_3 \\ \xi_4^2 & \eta_4^2 & \xi_4 & \eta_4 \end{vmatrix}$$

-continued $$\frac{(x-\xi_0)^2}{r_x^2} + \frac{(y-\eta_0)^2}{r_y^2} = 1 \qquad \text{Equation 8}$$

$$\xi_0 = -\frac{D}{2A}$$

$$\eta_0 = -\frac{E}{2C}$$

$$r_x = \sqrt{-\frac{F}{A} + \frac{D^2}{4A^2} + \frac{E^2}{4AC}}$$

$$r_y = \sqrt{-\frac{F}{A} + \frac{D^2}{4AC} + \frac{E^2}{4C^2}}$$

The ellipse center calculation part 83 selects four points—Q1 ($\xi_1$, $\eta_1$), Q2 ($\xi_2$, $\eta_2$), Q3 ($\xi_3$, $\eta_3$), and Q4 ($\xi_4$, $\eta_4$)—from the partial tomographic image data extracted by the housing extraction part 81. Then, the ellipse center calculation part 83 calculates each value of coefficients—A, C, D, E, and F—of Equation 6 by applying the coordinate values of these four points—Q1 ($\xi_1$, $\eta_1$), Q2 ($\xi_2$, $\eta_2$), Q3 ($\xi_3$, $\eta_3$), and Q4 ($\xi_4$, $\eta_4$)—to each equation in Equation 7, and it calculates the coordinates ($\xi_0$, $\eta_0$) of the center K by substituting the coefficient values to the second and third equations in Equation 8.

Displacement Calculation Part

The displacement calculation part 84 relates to an example of the "displacement calculation unit," "the first displacement calculation unit," and "the second displacement calculation unit" of the invention. The displacement calculation part 84 calculates displacement of the cylinder axis J of the phantom 100 relative to the center O of the scan (rotation center of the X-ray tube 22 and X-ray detector 23), based on the calculation result by the circle center calculation part 82 or the results calculated by the ellipse center calculation part 83.

Action of the displacement calculation part 84, based on the results of calculation by the circle center calculation part 82, will be described. The circle calculation part 82, as described above, selects the three points—P1, P2, and P3—from the partial tomographic image data extracted by the housing extraction part 81, and it calculates the coordinates of the center C of the circle, which passes through these three points—P1, P2, and P3 (refer to FIG. 5A, FIG. 5B, and FIG. 6). The displacement calculation part 84 calculates displacement ($\Delta x$, $\Delta y$) of the cylinder axis J of the phantom 100 relative to the center O of the scan, based on the calculated coordinates of the center C of the circle and the rotation center information 73 that is stored in the data storage part 72.

A specific example of the calculation process will be described below. Here, the coordinates of the center C of the circle are set to ($x_0$, $y_0$), and the coordinates of the center O of the scan indicated in the rotation center information 73 are set to (255, 255). The displacement calculation part 84 obtains displacement $x_0$-255 of the X direction and displacement $y_0$-255 of the Y direction of the center C relative to the center O of the scan. If the gradient of the cylinder axis J of the phantom 100 relative to the slice direction (Z direction) is so small that it can be ignored, the tomographic image 101A on the case 101 becomes nearly a circular shape. Therefore, displacement ($\Delta x$, $\Delta y$) of the cylinder axis J of the phantom 100 relative to the center O of the scan becomes nearly the same as the abovementioned calculated results ($x_0$-255, $y_0$-255). In addition, whether the level of gradient of the cylinder axis J of the phantom 100 can be ignored coincides with whether the level of gradient of the phantom 100 can be ignored, and it is determined by the error processing part 90 to be described later.

Next, action of the displacement calculation part 84, based on the calculated results from the ellipse center calculation part 83, will be described. The ellipse calculation part 83, as described above, selects the four points—Q1, Q2, Q3, and Q4—from the partial tomographic image data extracted by the housing extraction part 81, and it calculates the coordinates of the center K of the ellipse, which passes through these four points—Q1, Q2, Q3, and Q4 (refer to FIG. 7). The displacement calculation part 84 calculates displacement ($\Delta\xi$, $\Delta\eta$) of the cylinder axis J of the phantom 100 relative to the center O of the scan, based on the calculated coordinates of the center K of the ellipse and the rotation center information 73.

A specific example of the calculation process will be described below. Here, coordinates of the center K of the ellipse are set to ($\xi_0$, $\eta_0$), and coordinates of the center O of the scan indicated in the rotation center information 73 are set to (255, 255). The displacement calculation part 84 obtains displacement $\xi_0$-255 of the X direction and displacement $\xi_0$-255 of the Y direction of the center K relative to the center O of the scan.

Radius Calculation Part

The radius calculation part 85 relates to an example of the "radius calculation unit" of the invention. The radius calculation part 85, as in the ellipse center calculation part 83, acts when a phantom 100 is positioned on a gradient relative to the slice direction (Z direction), and calculates the horizontal radius (X direction) and vertical radius (Y direction) of the ellipse passing through the four different points in the partial tomographic image data extracted by the housing extraction part 81. In addition, determination of whether a phantom 100 is inclined is performed by the error processing part 90 to be described later.

The radius calculation part 85 calculates the radius $r_x$ of the X direction of the abovementioned ellipse by substituting the coefficients—A, C, D, E, and F—obtained from the equations of Equation 7 to the fourth equation in Equation 8. Moreover, the radius calculation part 85 calculates the radius $r_y$ of the Y direction of the abovementioned ellipse by substituting the coefficients—A, C, D, E, and F—to the fifth equation in Equation 8.

Gradient Angle Calculation Part

The gradient angle calculation part 86 relates to an example of the "gradient angle calculation unit" of the invention. The gradient angle calculation part 86 calculates the angle of gradient of the cylinder axis J of the phantom 100 relative to the slice direction (Z direction), based on the horizontal radius $r_x$ (X direction) and the vertical radius $r_y$ (Y direction) of the ellipse calculated by the radius calculation part 85. This angle of gradient is also the angle of gradient relative to a rotation plane when the gantry 2 is not inclined.

In addition, the slice direction (Z direction) matches the normal direction of the rotation plane (scan plane, or slice plane) of the X-ray tube 22 and X-ray detector 23 that are rotated with the support 21 by the support drive part 25. In other words, the support 21 is driven so as to rotate within the predetermined plane (rotation plane) by the support drive part 25, and the slice direction is the normal direction of the predetermined plane, or in other words, the direction parallel to the direction of rotation axis of the support 21.

The angle of gradient $\Delta\theta$ of the cylinder axis J of the phantom 100 relative to the slice direction can be obtained by the following equation.

$$\Delta\theta = \cos^{-1}\left(\frac{r_y}{r_x}\right)$$ Equation 9

The gradient angle calculation part 86 obtains the angle of gradient Δθ of the cylinder axis J of the phantom 100 relative to the slice direction by substituting the radius $r_x$, $r_y$ of the ellipse calculated by the radius calculation part 85 in Equation 9.

Error Processing Part

The error processing part 90 performs processes related to errors relative to the circle in the tomographic image 101A (tomographic image 101A of the outer circumference surface) of the case 101 that is considered by the circle center calculation part 82. Moreover, the error processing part 90 performs processes related to errors relative to the ellipse in the tomographic image (tomographic image 101b of the outer circumference surface) of the case 101 that is considered by the ellipse center calculation part 83. In the error processing part 90, the following types of error calculation parts 91 and error assessment parts 92 are set.

Error Calculation Part

The error calculation part 91 relates to an example of the "error calculation unit" of the invention. The error calculation part 91, as its first process, selects multiple points on the partial tomographic image data (image data of a tomographic image 101A on the case 101 of the phantom 100) extracted by the housing extraction part 81, and performs the process of calculating error of the multiple points relative to the circle considered by the process of the circle center calculation part 82 (refer to Equation 2). The average error indicated by the following equation, for example, is used as this error.

$$AveError = \frac{\sum_{i=1}^{N}\left|\left(\sqrt{(x_i - x_0)^2 + (y_i - y_0)^2}\right) - r\right|}{N}$$ Equation 10

It is indicated in here that $x_0$ is the X coordinate of the center C of the circle, $y_0$ is the Y coordinate of the center C, and r is the radius of the circle (refer to Equation 3). Moreover, N indicates the number of samples (that is, the abovementioned multiple points) in partial tomographic image data in a calculation of average error. This sample number N is, for example, in a range of 10-100.

Selection of the sample (multiple points) taken for the calculation of average error is conducted accordingly. For example, average error may be calculated by using all of the pixels (all points) that form a partial tomographic image data. Furthermore, selection of every 5$^{th}$ pixel among pixels that form a partial tomographic image, for example, is possible, and multiple pixels may be selected for calculation of average error. Generally, a large number of samples should be selected if accuracy of the average error calculation is emphasized. Conversely, if processing time of calculation and/or CPU resources are emphasized, a relatively small number of samples can be selected.

The tomographic image 101A on the case 101 (tomographic image 101a on the outer circumference surface) shown in FIG. 5A, FIG. 5B, and FIG. 6 does not become a circle when, for example, the phantom 100 is positioned on a gradient. The average error in Equation 10 is used as an indicator showing how much the tomographic image 101A (101a) differs from a circle.

The error calculation part 91, as part of its second process, selects multiple points on the partial tomographic image data extracted by the housing extraction part 81, and calculates error of the multiple points relative to the ellipse considered by the process of the ellipse center calculation part 83 (refer to Equation 8). The average error indicated by the following formula, for example, is used as this error.

$$AveError = \frac{\sum_{i=1}^{N}\left|\left(\sqrt{\frac{(x_i - \xi_0)^2}{r_x^2} + \frac{(y_i - \eta_0)^2}{r_y^2}}\right) - 1\right|}{N}$$ Equation 11 wherein, $\xi_0$ indicates the X-coordinate of the ellipse center K, $\eta_0$ indicates the Y-coordinate of the center K, $r_x$ indicates the radius in the X-direction and $r_y$ indicates the radius in the Y direction (refer to Equation 8). N indicates, as in Equation 10, the number of samples in the tomographic image data for calculating the average error (that is, the plural points mentioned above).

The average error in Equation 11 is an index showing how far the tomographic image 101b of the outer surface of the case 101 shown in FIG. 7 is displaced from the ellipse that is considered in a process of an ellipse center calculation part 83.

(Error Determination Part)

An error determination part 92 relates to an example of the "determination unit" of the invention. The error determination part 92 determines whether the error (average error) calculated by the error calculation part 91 exceeds a predefined value. In this embodiment, a "predefined value" is a threshold value of the average error shown in Equation 10 and Equation 11, which is, for example, "threshold value=1.0". The threshold value is included in the error information 74 of a data storage part 72. The error determination part 92 determines whether the average error is higher or lower than the threshold value by comparing the average error value calculated by the error calculation part 91 to the threshold value (=1.0) indicated in the error information 74.

Action

The action of an X-ray CT apparatus 1 related to the embodiment with the above composition is described with reference to the flow chart in FIG. 8. The action of each part of the X-ray CT apparatus 1 is conducted based on control of an apparatus control part 41.

First, an operator mounts the phantom 100 on a top plate 31 of the bed 3 (S1). When mounting the phantom 100, it is preferable to make sure that the cylinder axis J of the phantom 100 is positioned in the center of the scan, and the cylinder axis J is adjusted to be in the slice direction (Z-direction).

Then, tomographic image data for the phantom 100 is generated by operating the X-ray CT apparatus 1 (S2). Specifically, the gantry 2 collects data on the dose of X-rays that are transmitted through the phantom 100 to send it to the computer apparatus 4, and a tomographic image data generating part 60 generates tomographic image data for the phantom 100. The generated tomographic image data is stored in the image storage part 71. The image (reconstructed image) based on the tomographic image data is a tomographic image of the phantom 100, as shown in FIG. 5A.

This is then followed by processing by the calculation processing part 80. First, the housing extraction part 81 retrieves the tomographic image data to be analyzed from the image storage part 71, and extracts the tomographic image data (partial tomographic image data) of the corresponding part to the case 101 of the phantom 100 (S3). The image based on the extracted partial tomographic image data is a tomographic image on the case of the phantom 100 as shown in FIG. 5.

Then, the apparatus control part 41 selectively operates the circle center calculation part 82. The circle center calculation part 82 selects three points, P1 $(x_1, y_1)$, P2 $(x_2, y_2)$ and P3 $(x_3, y_3)$, from the partial tomographic image data, and calculates the coordinates of the center C of a circle passing through the three points, P1, P2 and P3 $(x_0, y_0)$ (S4).

Then, the displacement calculation part 84 calculates the displacement of the cylinder axis J of the phantom 100 relative to the center O of the scan, $(\Delta_x, \Delta_y) = (x_0-225, y_0-255)$, based on the calculated coordinates $(x_0, y_0)$ of the center C of the circle and the coordinates (255, 255) of the center O of the scan indicated in the rotation center information 73 in data storage 72 (S5).

Then, the apparatus control part 41 operates the error processing part 90. The error calculation part 91 selects plural points on the partial tomographic image data extracted in step S3, and calculates the average error of the plural points relative to the considered circle (a circle passing through the three points, P1, P2 and P3) in the process of step S4 (S6).

Furthermore, the error determination part 92 refers to the error information 74 stored in the data storage 72 to determine whether the average error value calculated in step S6 exceeds the threshold value (=1.0) shown in the error information 74 (S7).

(When the Average Error Value does not Exceed the Threshold Value)

When the average error value does not exceed the threshold value (S7; N), the apparatus control part 41 displays displacement $(\Delta_x, \Delta_y)$ of the phantom 100 that is calculated in step S5 on the screen of a monitor 5 (S8). The display process is performed by a console control part 53.

Here, an example of the display form for displacement of the phantom 100 is described. Firstly, a displacement value can be displayed itself, for example, "Vertical error: 10 mm, Horizontal error: −5 mm" (refer to the coordinate axis in FIG. 6). As shown in FIG. 6, a graphic display of the position of the center C relative to the center O of a scan is also possible.

Another display form, in which the direction of displacement is clearly specified, may also be employed. That is, based on the definition of the direction of the X-coordinate axis shown in FIG. 6, when displacement in the X-direction $\Delta_x$ is positive (+), displacement of the phantom 100 to the right is displayed, and when it is negative (−), displacement to the left is displayed. Moreover, based on the definition of the direction of the Y-coordinate axis shown in FIG. 6, when displacement in the Y-direction $\Delta_y$ is positive (+), downward displacement of the phantom 100 is displayed, and when it is negative (−), upward displacement is displayed. As an example, a dialog box with a message, "Vertical error: 10 mm downward, Horizontal error: 5 mm to the left", may be displayed.

In addition, instead of displaying the direction of displacement of the phantom 100 as described above, the direction in which the phantom 100 should be moved may be displayed. In other words, when displacement in the X-direction $\Delta_x$ is positive (+), the display may indicate that the phantom 100 should be moved to the left in FIG. 6, and when it is negative (−), the display may indicate that Phantom 100 should be moved to the right, and when displacement in the Y-direction $\Delta_y$ is positive (+), the display may indicate that the phantom 100 should be moved upwards, and when it is negative (−), the display may indicate that the phantom 100 should be moved downwards. As an example, a dialog box with a message, "Vertical movement: 10 mm upward, Horizontal movement: 5 mm to the right", may be displayed. As above, displaying the direction in which the phantom 100 should be moved is also considered to be "Displacement display".

Refer to the flow chart in FIG. 8 again. An operator refers to the displacement of the phantom 100 displayed in the monitor 5, and places the cylinder axis J on the center O of a scan by operating an input device 6 to adjust the location of the top plate 31 of the bed 3 (S9).

Now, the operation for positioning the phantom 100 is completed. The operator can start a process of performance evaluation for the X-ray CT apparatus 1.

(When the Average Error Value Exceeds the Threshold Value)

When the average error value that was calculated in step S6 exceeds the threshold value (S7; Y), the apparatus control part 41 operates both the ellipse center calculation part 83 and the radius calculation part 85. The processes of the ellipse center calculation part 83 and radius calculation part 85 as well as the subsequent processes of the displacement calculation part 84 and the gradient angle calculation part 86, described below, may be conducted in any order. Moreover, some of these processes may be conducted in parallel.

The ellipse center calculation part 83 selects four points, Q1 $(\xi_1, \eta_1)$, Q2 $(\xi_2, \eta_2)$, Q3 $(\xi_3, \eta_3)$ and Q4 $(\xi_4, \eta_4)$ that were extracted in step S3 to calculate the coordinates $(\xi_0, \eta_0)$ of the center K of the ellipse passing through the four points, Q1, Q2, Q3 and Q4 (S10).

Then, the displacement calculation part 84 calculates the displacement of the cylinder axis J of the phantom 100 relative to the center O of the scan, $(\Delta\xi, \Delta\eta) = (\xi_0-225, \eta_0-255)$, based on the calculated coordinates $(\xi_0, \eta_0)$ of the center K of the ellipse and the coordinates (255, 255) of the center O of a scan indicated in the rotation center information 73 (S11).

Meanwhile, the radius calculation part 85 calculates the radii of the ellipse passing through the four points, Q1, Q2, Q3 and Q4, which are $r_x$ in the horizontal direction (X-direction) and $r_y$ in the vertical direction (Y-direction) (S12).

Furthermore, the gradient angle calculation part 86 calculates gradient angle $\Delta\theta$ of the cylinder axis J of the phantom 100 relative to the slice direction (Z-direction), based on the calculated radius $r_x$ of the ellipse in the horizontal direction (X-direction), and the radius $r_y$ in the vertical direction (Y-direction) (S13).

Then, the apparatus control part 41 operates the error processing part 90 again. The error calculation part 91 selects plural points from the partial tomographic image data extracted in step S3, and calculates the average error of the plural points relative to the considered ellipse (an ellipse passing through the four points, Q1, Q2, Q3 and Q4) in the process of step S10 (S14).

Then, the error determination part 92 refers to the error information 74 stored in the data storage part 72 to determine whether the average error value calculated in step S14 exceeds the threshold value (=1.0) indicated in the error information 74 (S15).

When the average error value does not exceed the threshold value (S15; N), the apparatus control part 41 displays the displacement $(\Delta\xi, \Delta\eta)$ of the phantom 100 calculated in step S11, and the gradient angle calculated in step S13 $\Delta\theta$, on the screen of the monitor 5 (S16).

A display form of the displacement $(\Delta\xi, \Delta\eta)$ of the phantom 100 is the same as the displacement $(\Delta_x, \Delta_y)$ in the description of step S8. As for the gradient angle Δθ, a message such as "Error in the gradient direction: 3 degrees" may be displayed.

The operator may refer to the displacement of the phantom 100 displayed on the monitor 5, and place the cylinder axis J of the phantom 100 on the center O of a scan by operating the input device 6 to adjust the location of the top plate 31 in the bed 3 and the tilt angle of the gantry 2 (S17).

Now, the operation for positioning the phantom 100 is completed. The operator can start the process of performance evaluation for the X-ray CT apparatus 1.

Meanwhile, when the average error value exceeds the threshold value (S15; Y), the apparatus control part 41 displays a warning message on the monitor 5 (S18). The warning message includes information on any failure to effectively obtain the displacement or gradient angle of the phantom 100, and/or requests for re-mounting of the phantom. The operator conducts operations in compliance with the warning massage.

This is the end of the positioning operation for a phantom in the X-ray CT apparatus 1 in reference to the embodiment. Modified embodiments for the positioning operation of a phantom are described below.

Function and Advantage

According to the embodiments of the X-ray CT apparatus 1 described above, the following functions and advantages can be obtained.

At first, according to the X-ray CT apparatus 1, for the phantom 100 mounted on the top plate 31 of the bed 3, displacement from the center O of the scan of the cylinder axis J is calculated automatically to be displayed, and thereby, the operator can easily understand displacement of the cylinder axis J relative to the center O of the scan. Therefore, regardless of the skill of the operator, placement of the cylinder axis J onto the center O of a scan can be done easily and quickly. Herein, instead of displaying the obtained displacement as it is, information for placement of Phantom 100 based on the displacement (messages such as "Move phantom . . . centimeter to . . . direction") may be displayed.

It also functions to calculate the gradient angle of the phantom 100 automatically for displaying, so the operator can easily understand the gradient angle of the cylinder axis J relative to the slice direction. Therefore, regardless of the skill of the operator, placement of the cylinder axis J to be aligned with the slice direction can be done easily and quickly. Herein, instead of displaying the obtained gradient angle as it is, information for placement of Phantom 100 based on the gradient angle (massages such as "Incline phantom . . . centimeter ( . . . degree) to . . . direction") may be displayed.

The X-ray CT apparatus 1 determines whether the cylinder axis J of the phantom 100 has the gradient relative to the slice direction with significant level (Refer to step S7 of the flow chart in FIG. 8), and alters contents of a process depending on the determination result.

More specifically, when a gradient of the phantom 100 is negligible level (S7; N), the tomographic image of the cylindrical phantom 100 is an approximate circle, therefore, the location of the center of the circle passing through three points in the case 101 part is considered to approximate the location of the cylinder axis J of the phantom 100. The X-ray CT apparatus 1 obtains displacement of approximate location of the cylinder axis J (center of the circle), relative to the center O of the scan that is known. Consequently, when a gradient of the phantom 100 is negligible level, the displacement of the cylinder axis J relative to the center O of the scan can be obtained with high accuracy.

Meanwhile, when a gradient of the phantom 100 is significant level (S7; Y), the tomographic image of the cylindrical phantom 100 is elliptical, therefore, the center location of the center of the ellipse passing through four points in the case 101 part is considered to approximate the location of the cylinder axis J of the phantom 100. The X-ray CT apparatus 1 obtains displacement of approximate location of the cylinder axis J (center of the ellipse), relative to the center O of the scan that is known. It also obtains the gradient angle of the approximate cylinder axis based on radii of said ellipse in X-direction and Y-direction. Consequently, when a gradient of the phantom 100 is significant level, both the displacement of the cylinder axis J relative to the center O of the scan, and the gradient angle of the cylinder axis J relative to the slice direction, can be obtained with high accuracy.

Besides, when a gradient of the phantom 100 is significant level, sometimes no elliptical tomographic image can be obtained for some reasons. For example, if the cylinder axis J of the phantom 100 has a large gradient angle relative to the slice direction, both ends of the phantom 100 is placed to intersect with the rotation plane of an X-ray tube 22, so a tomographic image becomes rectangle-like (When the cylinder axis J intersects with the slice direction at a right angle, a rectangular tomographic image is obtained. Or, when an angle of the cylinder axis J and the slice direction is close to a right angle, an approximate rectangular tomographic image, expanded in the middle, can be obtained.). In order to respond in such a case, the X-ray CT apparatus 1 makes a determination if the tomographic image can be considered as an ellipse (S15). When it can be considered as an ellipse, (S15; N), the displacement and the gradient angle, which is calculated based on the above-mentioned ellipse passing through the four points, is displayed. On the contrary, if it cannot be considered as an ellipse (S15; Y), caution and another operation are encouraged by displaying a warning massage. Consequently, accuracy of display contents can be secured.

Modified Embodiments

Regarding the embodiment of the X-ray CT apparatus 1, various modified embodiments will be described. The modified embodiments regarding this embodiment can be applied accordingly to the second and the third embodiments to be described below. Additionally, a composition of any two or more of the following modified embodiments can be applied as well.

Modified Embodiment 1

When a gradient of the phantom 100 is significant level (S7; Y), a message to indicate that the phantom 100 tilts or to encourage a correction of the gradient may be displayed on the monitor 5. By referring to the warning message, the operator can recognize that the phantom 100 tilts in no small measure, and also the necessity for correction of it. Thereby, the operation can be eased and accelerated.

The warning message displayed when a gradient of the phantom 100 is significant level (S7; Y) or when a tomographic image of the phantom 100 cannot considered as an ellipse (S15; Y), relates to an example of the "alarm information" of the invention. The alarm information is not limited to such warning message, and any form may be applied as long as the above determination result can be made known by the information. The form may be visual information, such as by lighting (blinking) of a warning lamp, audio information such as a warning buzzer, and tactile information such as vibration of a device carried by an operator.

Such alarm information is an output controlled by the console control part 53 in the apparatus control part 41. The console control part 53 relates to an example of the "alarm information output device" of the invention.

Modified Embodiment 2

In the embodiment, it is possible to apply a composition to calculate a gradient direction of the phantom 100. A tomographic image of the phantom 100 is elliptical shape with the major axis in the gradient direction. For example, in the tomographic image 100B described in FIG. 7, Y-direction is the major axis, that means the phantom 100—tilts in the vertical direction.

Consequently, when a tomographic image with an elliptical shape is obtained, for example, by analyzing the image, the direction of the major axis is obtained (such as an angle relative to X-coordinate or Y-coordinate). The direction is the gradient direction of the phantom 100. As for the gradient direction, based on a radius in the gradient direction (a radius in the major axis direction) and a radius in the direction that intersects with the gradient direction at a right angle (a radius in the minor axis direction), it can be obtained in the same way as the equation in Equation 9. The obtained gradient direction is displayed on the monitor 5. As a display form, such as a text display indicating a gradient direction (e.g., "Direction with a 10-degree angle in the vertical direction"), or a graphic display can be applied.

Modified Embodiment 3

In this modified embodiment, a gradient direction of the phantom 100 is obtained with a different method from in the above Modified Embodiment 2. In this embodiment, the following processes are conducted: (1) generating plural tomographic image data at different slice positions of the phantom 100; (2) identifying a gradient direction of the cylinder axis J in the phantom 100, based on the plural tomographic image data; (3) displaying the identified gradient direction on the monitor 5. Hereafter, an illustrative embodiment of contents of processes in Process (1)-(3) is described, and then an illustrative embodiment with two slice positions is described.

(1) An X-ray scanning is performed on the phantom 100 using the gantry 2. Herein, the phantom 100 is scanned at plural different slice positions by being moved the top plate 31. Scanning may be performed at any number of slice positions (Z-coordinate value). As for scan forms, scanning intermittently at plural slice positions by alternatively repeating shifting the top plate 31 and scanning, or scanning continuously at plural slice positions as a helical scan, may be performed. Based on the result of scanning at each slice position, the tomographic image data generating part 60 generates each tomographic image data corresponding to each slice position.

(2) The housing extraction part 81 in the calculation processing part 80 analyses each of the generated plural tomographic image data to extract partial tomographic image data corresponding to the case 101 of the phantom 100. Then, the ellipse center calculation part 83 calculates the coordinates of the center of the ellipse passing through different four points, for each of generated plural partial tomographic image data. Then, based on the coordinates of the center of ellipses at these plural slice positions and coordinates of said plural slice positions, the calculation processing part 80 identifies a gradient direction of the phantom 100. Wherein, by considering intervals (distances) between the plural slice positions, a gradient angle of the phantom 100 can be calculated (to be described below).

The process (2) may be implemented by selecting at least two data from plural tomographic image data and using only the selected tomographic image data. That is, because the cylinder axis J of the phantom 100 is straight line, the centers of ellipses based on each tomographic image data are to be placed approximately in alignment. Therefore, by selecting two data from plural tomographic image data, the straight line connecting those will approximate the direction of the cylinder axis J. When selecting three or more tomographic image data, the optimal straight line, of which error relative to the each center of an ellipse is minimal, may be obtained using, for example, the least-square approach, and the process can be conducted by regarding it as the direction of the cylinder axis J.

(3) The console control part 53 displays identified gradient direction (and gradient angle) on the monitor 5. The gradient direction of the phantom 100 may be shown as a message display, for example, "Anterior end of phantom (end in +Z direction) is upward", or it can be shown as a graphic display.

Figure 9:
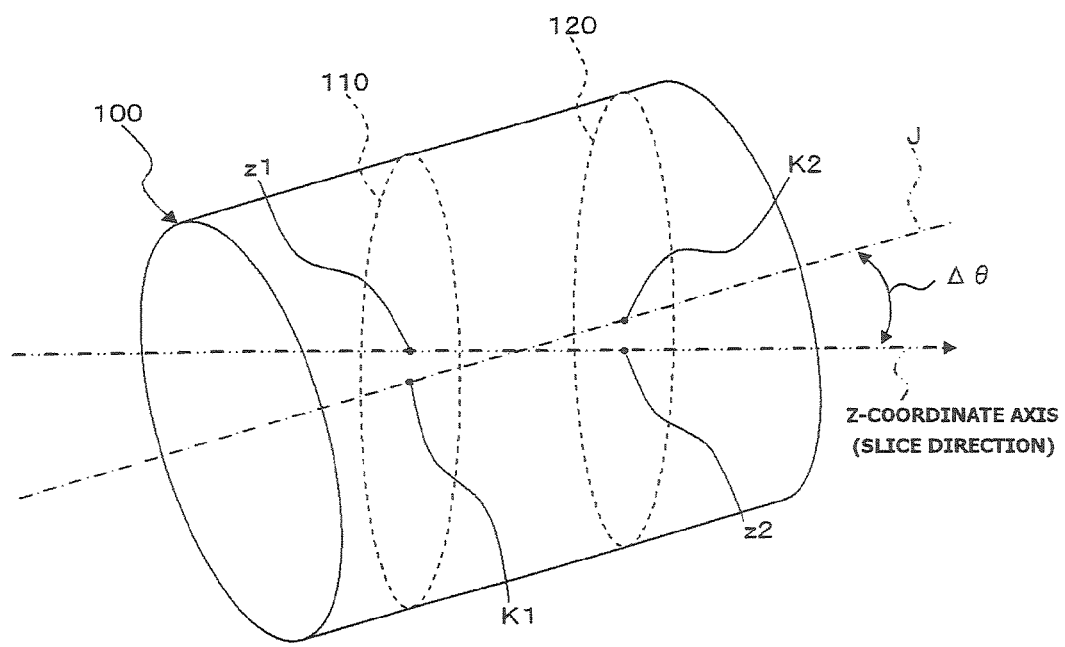
FIG. 9 is a schematic perspective view showing the phantom positioned in the gradient in a modified example 3 of the first embodiment of X-ray CT apparatus related to the invention.

(Illustrative Embodiment) Referring to FIG. 9, FIG. 10A and FIG. 10B, a case when generating tomographic image data at two slice positions will be described. The phantom 100 shown in FIG. 9 is placed with its end in +Z direction (anterior end) tilts upward (with its end in −Z direction (posterior end) tilts downward). The gradient angle of the cylinder J relative to Z-coordinate axis (slice direction) is $\Delta\theta$. For a simplified explanation, it is considered there is no gradient in the horizontal direction.

The two slice positions that generate tomographic image data are Z=z1 and z2 (z1<z2) herein. In each slice position of Z=z1 and z2, each cross section 110 and 120 of the phantom 100 is an ellipse with the major axis in the vertical direction (Y-direction) and the minor axis in the horizontal direction (X-direction).

Figure 10A:
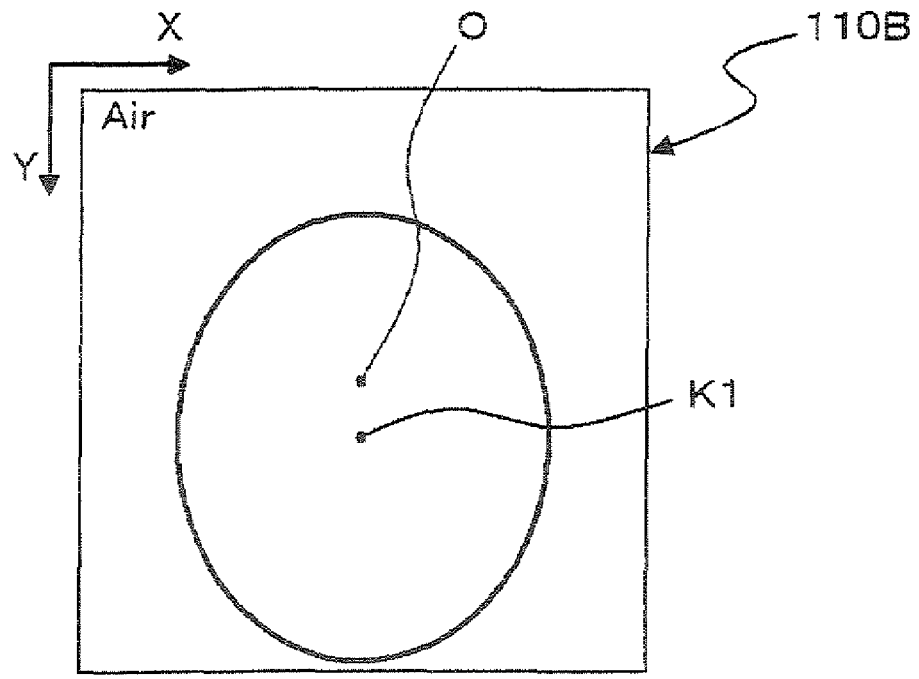
FIG. 10A is a schematic diagram showing a tomographic image of the phantom in the first slice position of the modified example 3 of the first embodiment of X-ray CT apparatus related to the invention.
Figure 10B:
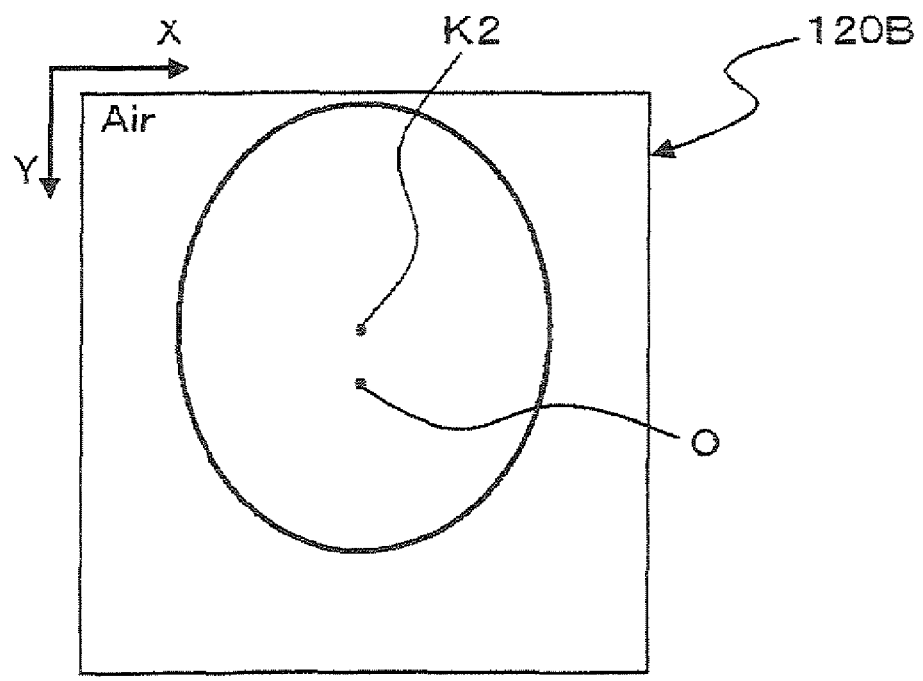
FIG. 10B is a schematic diagram showing a tomographic image in the second slice position of the modified example 3 of the first embodiment of X-ray CT apparatus related to the invention.

FIG. 10A represents tomographic image 110B showing the cross section 110 in the slice position Z=z1, and FIG. 10B represents tomographic image 120B showing the cross section 120 in the slice position Z=z2. In FIG. 9, FIG. 10A and FIG. 10B, the symbols K1 and K2 indicate the centers of tomographic images 110B and 120B of elliptical form calculated by the ellipse center calculation part 83, respectively.

The symbol O in FIG. 10A and FIG. 10B indicate the center of the scan. The coordinates of the center O of the scan is (X, Y)=(255, 255) as described above. The center O of the scan is identical to Z-coordinate axis as mentioned above. The center O of the scan in FIG. 10A is equated with the point at the intersection of the cross section 110B with Z-coordinate axis (z1 in FIG. 9), the center O of the scan in FIG. 10B is equated with the point at the intersection of the cross section 120B with Z-coordinate axis (z2 in FIG. 9)

Assuming that the coordinate of the center K1 of the tomographic image 110B at the first slice position Z=z1 is (X, Y)=(255, y1), and the coordinate of the center K2 of the tomographic image 120B at the second slice position Z=z2 is (X, Y)=(255, y2), then y1≠y2 because the phantom 100 is positioned with a gradient.

Considering that the relation between the first and second slice positions Z=z1 and z2 is z2>z1, the gradient direction of the phantom 100 is identified as follows: (A) If y2>y1, then it is concluded that the gradient direction of the phantom 100 has its anterior end tilting upward and posterior end tilting downward; (B) If y1>y2, then it is concluded that the gradient direction of the phantom 100 has its anterior end tilting downward and posterior end tilting upward.

In cases shown in FIG. 9, FIG. 10A and FIG. 10B, because the Y-coordinate y1 of the center K1 of the tomographic image 110B is smaller than the Y-coordinate y2 of the center K2 of the tomographic image 120B, then it is equivalent to above (A) case.

In the illustrative embodiment above, the case when the phantom 100 tilts only in the vertical direction was discussed, but for the example in the case when it tilts only in the horizontal direction, by considering the X-coordinate of the center of an elliptical tomographic image at plural slice positions, a gradient direction in the horizontal direction relative to the slice direction (Z-coordinate) (e.g. right direction/left direction toward +Z direction) can be identified. When a gradient of the phantom 100 includes the vertical direction component (Y-direction component) and the horizontal direction component (X-direction component), by considering each direction component, a gradient direction of the phantom 100 can be identified.

(Calculation of a gradient angle) A calculation process for a gradient angle $\Delta\theta$ of the phantom 100, mentioned in the above process (2), will be described. Information to be the basis for the calculation process for a gradient angle is coordinates of the center of ellipses of tomographic images at plural slice positions and coordinates of said plural slice positions. Also, two of the plural slice positions may be selected to be processed.

Now an explanation in concrete terms will be given with reference to FIG. 9, FIG. 10A and FIG. 10B. The calculation processing part 80 calculates an interval (distance) $\delta z=|z1-z2|$ between two slice positions Z=z1 and z2. It also calculates an interval (distance) $\delta=|y1-y2|$ between the centers of ellipses K1 (255, y1) and K2 (255, y2) of tomographic images 110B and 120B at two slice positions Z=z1 and z2. Hence, a gradient angle $\Delta\theta$ is calculated by the following equation.

$$\Delta\theta = \tan^{-1}\left(\frac{\delta}{\delta z}\right) \qquad \text{Equation 12}$$

Generally, when assuming coordinates of the centers of ellipses, K1 and K2 are (x1, y1) and (x2, y2), then the interval between K1 and K2 becomes $\delta=\sqrt{\{(x1-x2)^2+(y1-y2)^2\}}$.

Instead of the calculation process using Equation 9 in the above-mentioned embodiment, the calculation process for a gradient angle described herein can be conducted.

Modified Embodiment 4

In the embodiment, after calculating the coordinates of the center of a circle passing through three points corresponding with the case 101 of the phantom 100 (S4), and calculating displacement of the phantom 100 based on it (S5), the average error is determined (S7), however, the invention is not confined to this.

For example, based on the partial tomographic image data extracted in step S3, average error is calculated to be compared with the threshold value at first, and only if the average error is equal to or less than the threshold value, can it comprise calculation for the coordinates of the center of the circle and displacement of the phantom 100. This enables an omission of some processes such as calculation for the coordinates of the center of the circle, and thereby accelerating the process.

Modified Embodiment 5

The embodiment allows an operator to recognize the displacement and/or the gradient angle of the phantom 100 by displaying on a monitor. Wherein, a means of informing the operator, who recognizes the displayed contents, of the section of the input device 6 that should be operated, can be provided. Thereby, even when the operator is inexperienced, a situation where a wrong section is operated can be prevented.

The input device 6 is, as mentioned above, used for an operation to move the top plate 31 of the bed 3, or an operation to tilt the gantry 2, relates to the "top plate operation device" and the "tilt operation device" of the invention. The input device 6 provides a push button for a top plate operation that is to move the top plate 31, and a push button for a tilt operation that is to tilt the gantry 2 (both are not shown).

In this modified embodiment, for example, inside or underneath a push button for a top plate operation and a push button for a tilt operation, a light source such as LED (light emitting diode) is provided. The console control part 53 lights a LED inside a push button for a top plate operation when displaying only the displacement of the phantom 100 on the monitor 5 by supplying power to the input device 6. On the other hand, when displaying the displacement and the gradient angle of the phantom 100, it lights each LED inside a push button for a top plate operation and inside a push button for a tilt operation by supplying power to Input device 6. Thereby the section that should be operated in the input device 6 becomes apparent. Blinking of a light source may also inform the location of an operation button.

If a top plate operation device or tilt operation device is a software key displayed on the monitor 5, by lighting (blinking) the software key or changing its display color, the location may be informed. Location of an operation button or a software key may be informed with sound.

Modified Embodiment 6

Figure 8:
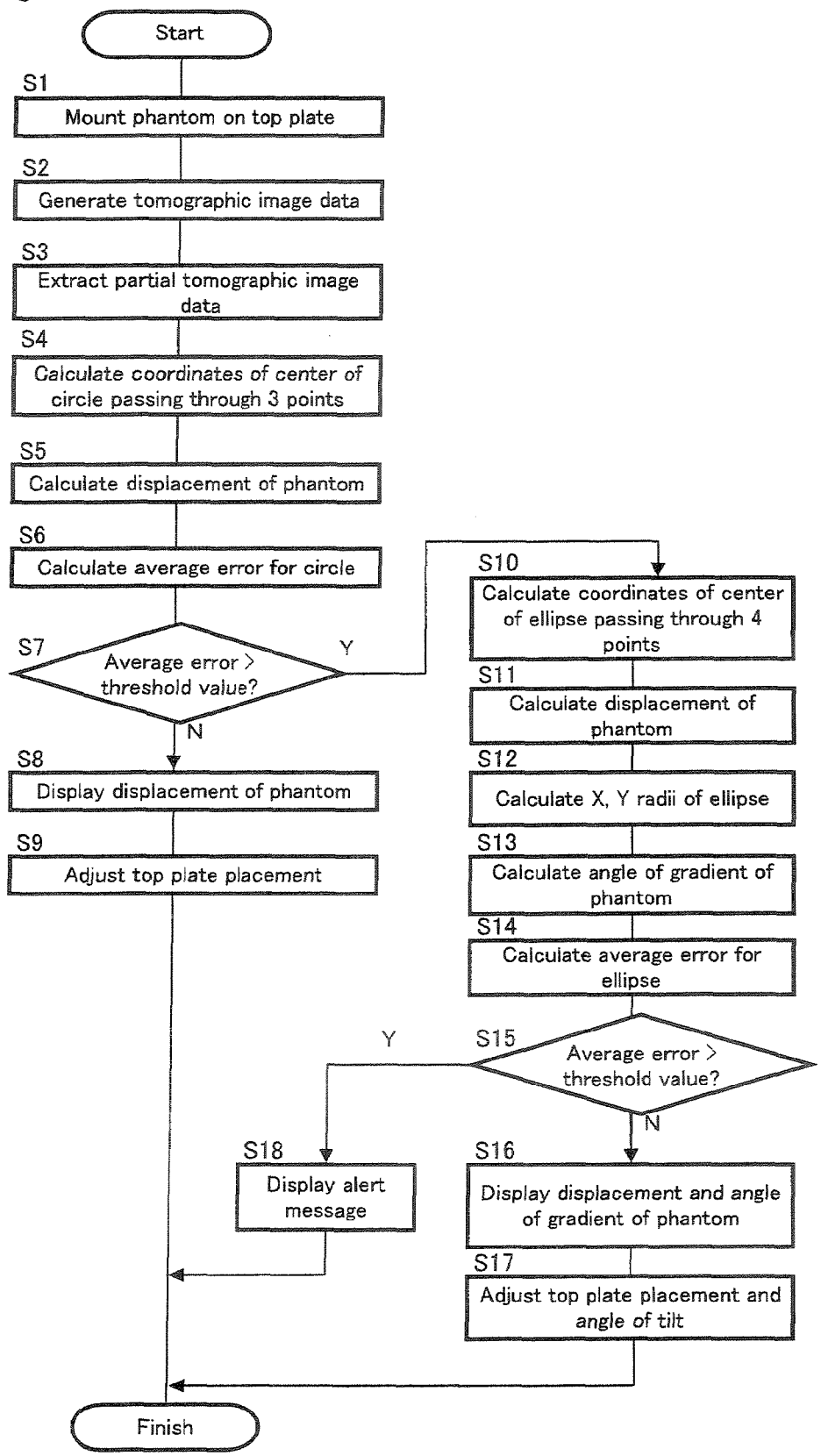
FIG. 8 is a flow chart showing an example of the action of the first embodiment of X-ray CT apparatus related to the invention.

As shown in the flow chart in FIG. 8, in the embodiment, the displacement of the phantom 100 relative to the center of a scan is calculated based on a circle passing through three points of a partial tomographic image data, and if an error of said partial tomographic image data relative to the circle is larger than the threshold value, based on the ellipse passing through four points of said partial tomographic image data, the displacement of the phantom 100 relative to the center of the scan and the gradient angle relative to the slice direction can be obtained.

Process with the X-ray CT apparatus regarding the invention is not limited to this, but it may be configured to conduct the following processes.

It is possible to configure to conduct a calculation process based on the ellipse passing through four points of a partial tomographic image data without conducting a calculation process based on the circle passing through three points of the partial tomographic image data. That is, it is possible to configure to conduct, following steps S1-S3 in FIG. 8, processes of steps S10 and after (it should include at least steps S10-S13 and S16). This is because, considering that a "circle" is a type of an "ellipse", a calculation result by the calculation process based on the circle as mentioned above can be obtained by the calculation process based on the ellipse as mentioned above.

Modified Embodiment 7

In the embodiment, when a calculation process based on the circle (steps S4-S6 in FIG. 8) is conducted, the circle passing through three points of a partial tomographic image data is used as said circle, however, the same process can be conducted using a circle passing through, for example, two points.

An example of a case using a circle passing through two points of a partial tomographic image data will be described. Out of three points P1-P3 shown in FIG. 6, the two points are used: the point of the smallest X-coordinate P1 and the point of the largest X-coordinate P2 (the point of the largest Y-coordinate P3 and the point of the smallest Y-coordinate may be used as well). The circle center calculation part 82 calculates coordinates of the midpoint between the point P1 and the point P2. The displacement calculation part 84 calculates displacement of the midpoint relative to the center O0 of the scan. The displacement of the midpoint is equal to the displacement of the center C of the circle relative to the center O of the scan calculated in the embodiment mentioned above.

In the same way, as for the calculation processes based on ellipses (step S10-S14 in FIG. 8), it is only necessary to consider two points on a partial tomographic image data to calculate the center K of the ellipse. For example, out of the four points Q1-Q4 shown is FIG. 7, by selecting the point of the smallest X-coordinate Q1 and the point of the largest X-coordinate Q2 to calculate the coordinate of the midpoint, the desired coordinates of the center K can be obtained.

If a gradient direction of the phantom 100 is in the horizontal direction or the vertical direction, by considering three points of a partial tomographic image data (e.g. Q1-Q3), a radius in the horizontal direction and a radius in the vertical direction can be calculated, and thereby a gradient angle can be calculated.

Modified Embodiment 8

The X-ray CT apparatus 1 in the embodiment is configured to calculate both displacement of a cylinder axis J of the phantom 100 relative to the center O of the scan and a gradient angle (gradient direction) of the cylinder axis J relative to the center O of a scan and display those, however, it may be configured to calculate only one of those to be displayed. It is also possible to enable a calculation only for coordinates of the center of a circle based on tomographic image data, or only for coordinates of the center of an ellipse.

Second Embodiment

In the first embodiment described above, the X-ray CT apparatus with a configuration of displaying results of calculation for displacement or a gradient angle of a phantom on a monitor was described. In the second embodiment described hereafter, the X-ray CT apparatus with a configuration of automatically adjusting a setting condition of a phantom based on results of calculation for displacement or a gradient angle of a phantom will be described.

The X-ray CT apparatus in this embodiment has the same configuration of the outer structure (Refer to FIG. 2), the inner structure (Refer to FIG. 3) and the control system structure (Refer to FIG. 4) as in the first embodiment. Hereafter, reference will be made to these figures. The X-ray CT apparatus in this embodiment is indicated by the same symbol 1 as in the first embodiment.

Figure 11:
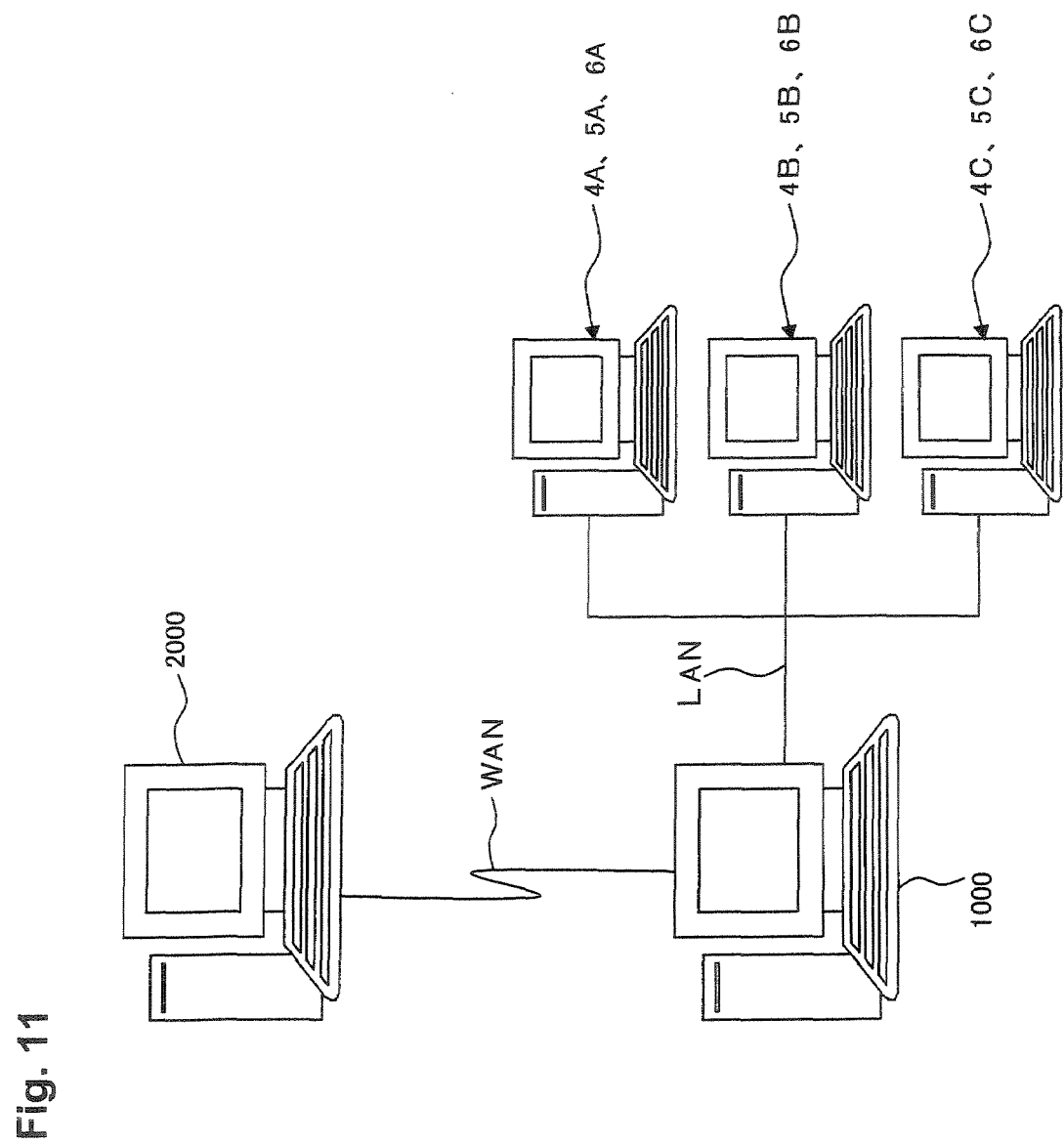
FIG. 11 is a schematic diagram showing an example of the composition of a maintenance system that performs maintenance of X-ray CT apparatus related to the invention.

Herein, a system of performing maintenance on the X-ray CT apparatus installed in such as plural medical institutions will be described. The skeleton framework of the maintenance system is shown in FIG. 11. For example, in each medical institute, one or more X-ray CT apparatus is installed (Three of those are installed in FIG. 11.).

The symbols 4A, 4B and 4C indicate the computer apparatus 4 of each X-ray CT apparatus. The symbols 5A, 5B and 5C indicate the monitor 5 of each X-ray CT apparatus 4A, 4B and 4C. The symbols 6A, 6B and 6C indicate Input device 6 of each X-ray CT apparatus 4A, 4B and 4C.

Each computer apparatus 4A, 4B and 4C is connected to the server device (Hospital server) 1000 through LAN in the medical institute. The hospital server 1000 analyzes image data of a captured image by the phantom 100 to calculate such as an average value and a standard deviation of CT value. Furthermore, the hospital server 1000 conducts a performance evaluation of the X-ray CT apparatus 1, for example, by comparing the calculation result with the correct value, and generates a report including the calculation result. The computer apparatus 4A-4C or a service server 2000 can be configured to perform all or part of the operations.

Hospital server 1000 in each medical institution is connected to the service server 2000 through WAN (Wide Area Network). The service server 2000 is located in such as a service center that provides maintenance service for the X-ray CT apparatus 1.

Each hospital server 1000, on the occurrence of predefined events, such as a failure of apparatus, an error occurrence and a deterioration of performance of apparatus, delivers information on the event or identification information of the X-ray CT apparatus 1 to the service server 2000. The service server 2000 receives information from the hospital server 1000 to inform a service provider. The service server 2000 accumulates the information delivered by the hospital server 1000 for analysis. The result of the analysis is used for, for example, a bug patch and research and development of the X-ray CT apparatus.

Figure 12:
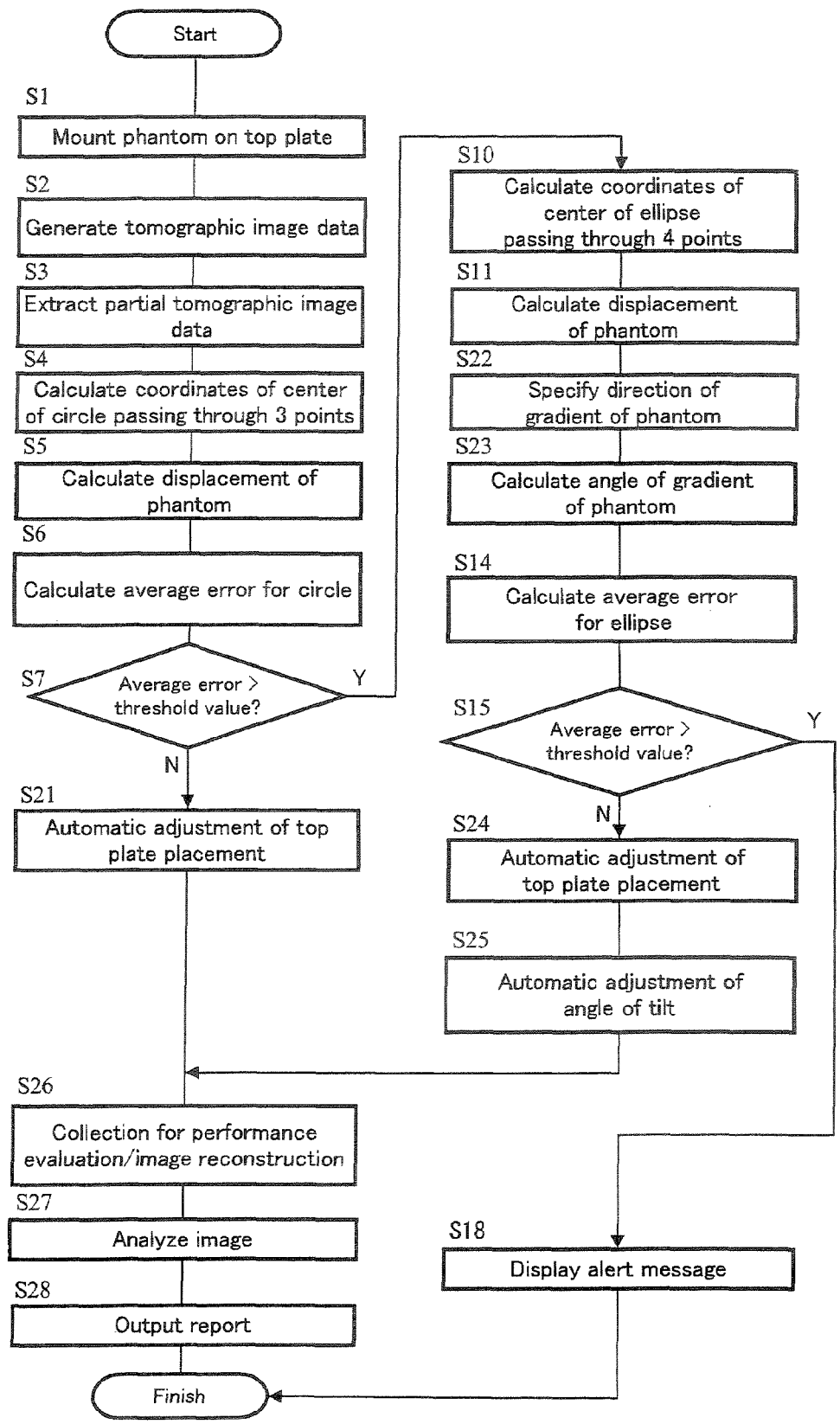
FIG. 12 is a flow chart showing an example of the action of the second embodiment of X-ray CT apparatus related to the invention.

An example of action of the X-ray CT apparatus 1 and service system is shown in FIG. 12. For the same steps as in the first embodiment, the same symbols are applied as in the flow chart in FIG. 8

Step S1 to step S7 are the same as in the first embodiment. In step S7, if determination is made that an average error is the threshold value or below (S7; N), the bed control part 52 controls the top plate drive part 33 based on the displacement calculated in step S5, and moves the position of the top plate 31 to negate said displacement, that is, to place a cylinder axis J on the center O of a scan (Z coordinate axis) (S21). More specifically, corresponding to displacement ($\Delta x$, $\Delta y$) of the cylinder axis J in the phantom 100 relative to the center O of the scan, the top plate 31 is moved ($-\Delta x$, $-\Delta y$).

Herein, movement of the top plate 31 in the vertical direction or the horizontal direction may be operated manually. In this case, it is preferred to display the result of calculation for the amount of displacement (and displacement direction) in the moving direction that is operated manually, on the monitor 5 as step S8 in FIG. 8. It is also preferred to be informed of the location of an operation button for manual input as the modified embodiment 5 of the first embodiment.

Once adjustment of the top plate location is completed, the X-ray CT apparatus 1 radiates X-ray toward the phantom 100 to gather projection data, as well as reconstructs an image of the phantom 100 (S26). The reconstructed image data is delivered to the hospital server 1000 through LAN.

The hospital server 1000 analyzes the image data of reconstructed image of the phantom 100, and conducts a performance evaluation on the X-ray CT apparatus 1 to generate a report (S27). The hospital server 1000 delivers the generated report to the X-ray CT apparatus 1 through LAN. Herein, if the evaluation result is not good, the hospital server 1000 delivers the evaluation result to the service server 2000 through WAN.

The X-ray CT apparatus 1 outputs the report received from the hospital server 1000 (S28). An example of output forms of reports is the display output to the monitor 5, and the print output by a printer (not shown). With that, the performance evaluation on the X-ray CT apparatus 1 using the phantom 100 is completed. An operator of the X-ray CT apparatus 1 can refer to the output report to perform various setting modifications of the X-ray CT apparatus 1.

If it is determined that the average error is larger than the threshold value in step S7 (S7; Y), as in the first embodiment, the coordinates of the center K of the ellipse passing through the four points is calculated (S11), and based on the coordinates of the center K of the ellipse and the coordinates of the center O of the scan, displacement of the cylinder axis J of the phantom 100 relative to the center O of the scan is calculated (S11).

Furthermore, by conducting the process described in the first embodiment and the process described in the modified embodiment 3, the gradient direction of the phantom 100 is identified (S22), and the gradient angle is also calculated (S23).

Then, the average error of partial tomographic image data relative to the said ellipse is calculated (S14) to be determined if the value exceeds the threshold value indicated in the error information 74 (S15).

If the value of the average error exceeds the threshold value (S15; Y), as in the first embodiment, a warning message is displayed (S18).

On the other hand, if the average error does not exceed the threshold value (S15; N), as in step S21 described above, the bed control part 52 controls the top plate drive part 33 based on the displacement calculated in step S11, and moves the top plate 31 to negate the said displacement (S24).

Moreover, the gantry control part 51 controls the support drive part 25, based on the gradient direction identified in step S22 and the gradient angle calculated in step S23, and tilts the support 21 (S25) to negate the gradient direction and the gradient angle, that is to align the normal direction of the rotation plane (scan plane) of the X-ray tube 22 and the X-ray detector 23 with the cylinder axis J of the phantom 100. Specifically, assuming the gradient angle is Δθ, and then the support 21 is tilted by Δθ degree to the opposite direction of the identified gradient direction. Thereby, the scan plane is placed in a direction perpendicular to the cylinder axis J.

Once adjustment of the location of the top plate and the angle of tilt are completed, the X-ray CT apparatus 1 gathers projection data by X-radiating the phantom 100, as well as reconstructs images of the phantom 100 (S26). The hospital server 1000 analyzes the image data of the reconstructed image of the phantom 100, and conducts a performance evaluation on the X-ray CT apparatus 1 to generate a report (S27). The X-ray CT apparatus 1 output the report generated by the hospital server 1000 (S28). With that, the performance evaluation on the X-ray CT apparatus 1 using the phantom 100 is completed.

According to this embodiment, for the phantom 100 mounted in the top plate 31 of the bed 3, it is configured to automatically calculate the displacement of the cylinder axis J relative to the center O of the scan, as well as to move the top plate 31 to align the cylinder axis J with the center O of the scan, and thereby an operator is not required to perform positioning of the cylinder axis J of the phantom 100 relative to the center O of the scan. Therefore, regardless of the skill of the operator, it is possible to position the phantom 100 easily and quickly.

Also for the gradient angle of the phantom 100 relative to the slice direction, it is configured to automatically calculate the gradient angle, as well as automatically tilt the rotation plane of the X-ray tube 22 and the X-ray detector 23 to position the X-ray scan plane by the gantry 2 in a direction perpendicular to the slice direction depending on the gradient angle, the operator is not required to conduct an adjustment operation for the gradient angle of the phantom 100. Therefore, regardless of the skill of the operator, it is possible to position the phantom 100 easily and quickly.

As in the first embodiment, it is configured to determine if the gradient angle of the phantom 100 can be ignored, and based on the result of the determination, modify the process contents, thereby both the displacement of the cylinder axis J relative to the center O of the scan and the gradient angle of the cylinder axis J relative to the slice direction can be obtained with high accuracy. Thereby, the top plate 31 and the angle of tilt can be automatically adjusted with good accuracy.

Additionally, as in the first embodiment, output of a warning message is possible.

Third Embodiment of the Invention

In the second embodiment mentioned above, the X-ray CT apparatus that controls the bed or the gantry based on the result of calculation for displacement or a gradient angle of the phantom was described. In the third embodiment to be mentioned below, the X-ray CT apparatus that adjusts the setting condition of the phantom by moving the phantom based on the result of calculation for displacement or a gradient angle of the phantom will be described.

Structure

Figure 13:
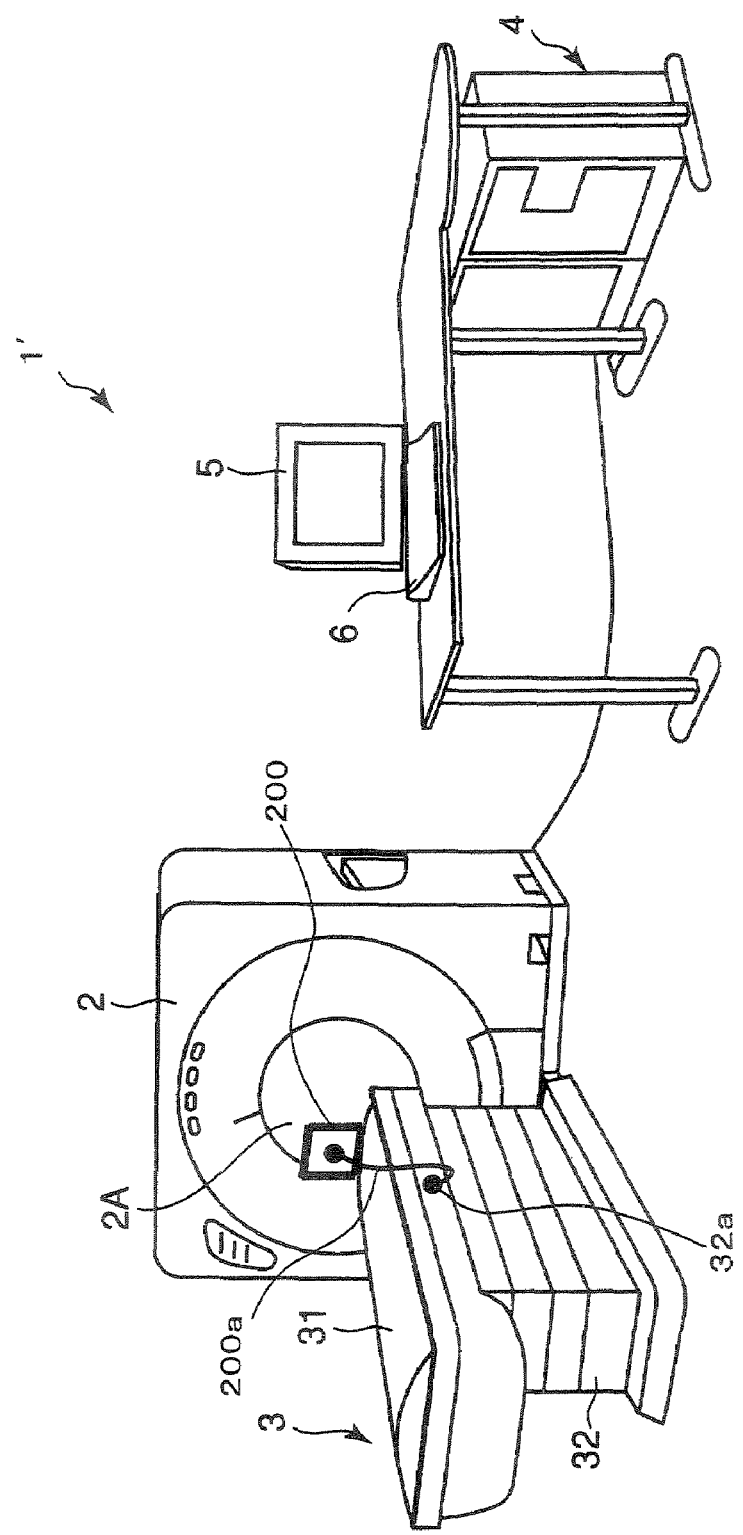
FIG. 13 is a schematic perspective view showing an example of the appearance of the composition of the third embodiment of X-ray CT apparatus related to the invention.
Figure 14:
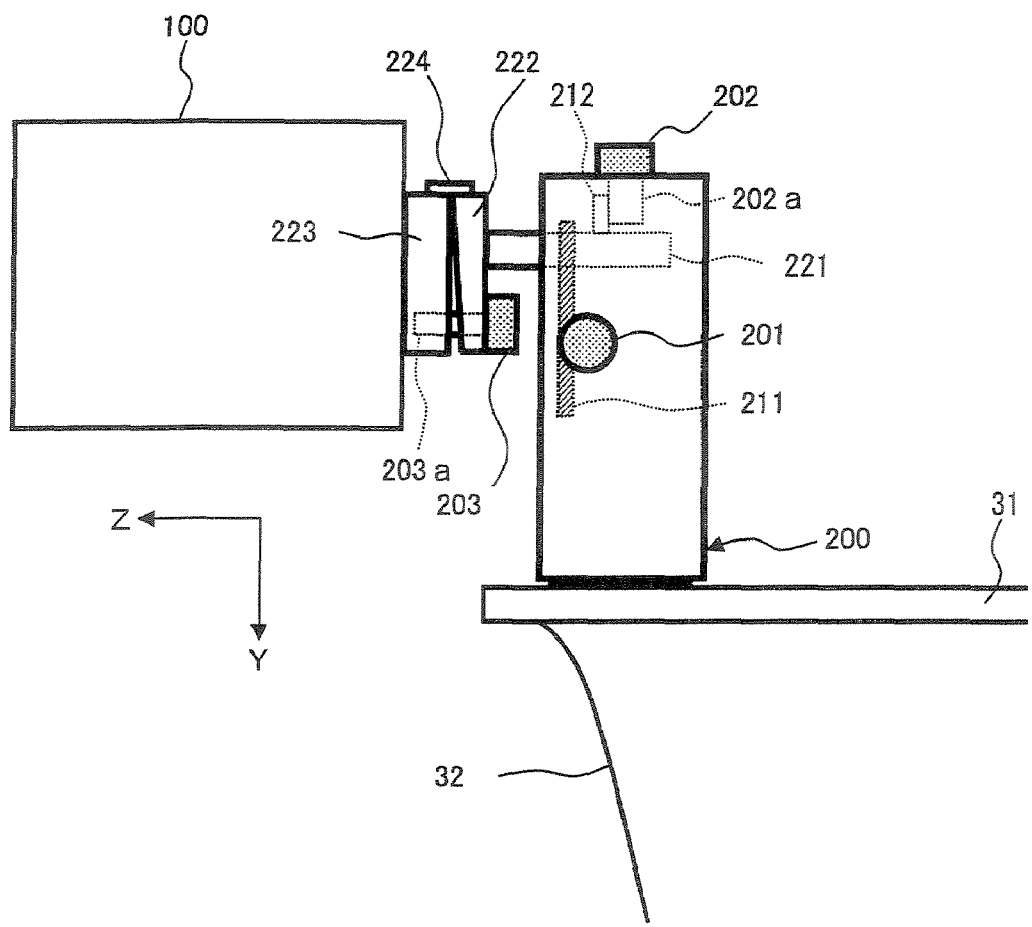
FIG. 14 is a schematic side-view showing an example of the composition of the phantom retaining tool of the third embodiment of X-ray CT apparatus related to the invention.
Figure 15:
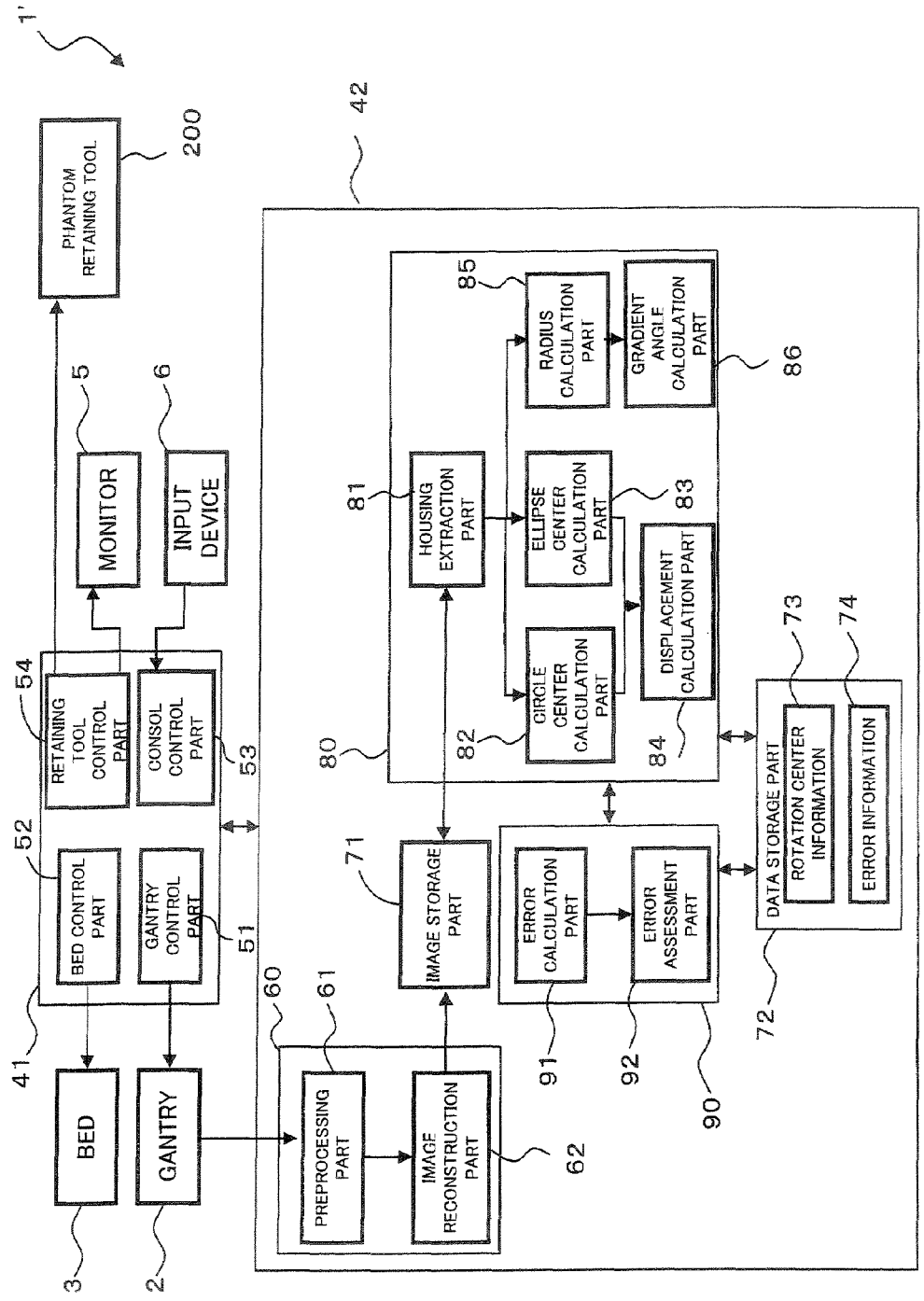
FIG. 15 is a schematic block diagram showing an example of the composition of the control system of the third embodiment of X-ray CT apparatus related to the invention.

Referring to FIG. 13, FIG. 14 and FIG. 15, the structure of an X-ray CT apparatus 1' in this embodiment will be described. The X-ray CT apparatus 1' has almost the same structure as in the first embodiment.

A phantom retaining tool 200 is an instrument to retain the phantom 100 on the top plate 31, which may be mounted on the top plate 31 of the X-ray CT apparatus 1' as shown in FIG. 13. The mounting form of the phantom retaining tool 200 relative to the top plate 31 is done using the conventional method. The phantom retaining tool 200 is, for example, mounted at the gantry 2 side of the end on the top plate 31, that is, at an end in a longitudinal direction of the top plate 31. The phantom retaining tool 200 relates to an example of "phantom retaining unit" of the invention.

To the surface of the opposite side of the gantry 2 of the housing for the phantom retaining tool 200, an end of a connection line 200a is connected. The other end of the connection line 200a is connected to a connector part 32a provided on the side surface of the bed base 32. When dismounting the phantom retaining tool 200 from the top plate 31, the connection line 200a should be removed from the connector part 32a.

The connection line 200a is to input an electronic signal into the phantom retaining tool 200 from the computer devise 4, and to provide an electric current to the phantom retaining tool 200 from an electric source (not shown). In this embodiment, the electric signal sent by the computer apparatus 4 passes through the gantry 2 and the bed base 32 to be input into the phantom retaining tool 200 via the connection line 200a.

The structure of the phantom retaining tool 200 will be described with reference to FIG. 14. The phantom 100 is mounted on a plate-like mounting part 223. The cylindrical phantom 100 is mounted with one end (i.e. one of the two circular surfaces) being in contact with one surface of the phantom mounting part 223.

A surface side of a plate-liked support part 222 is attached to the other side of the phantom mounting part 223. The top surface of the phantom mounting part 223 and the top surface of the support part 222 are attached to each other by a mounting member 224. The surface of the support part 222 in the phantom mounting part 223 tilts relative to the Y-direction (vertical direction). The bottom part of the phantom mounting part 223 and the bottom part of the support part 222 are attached to each other by a drive axis 203a of an actuator 203 to be described later.

To the other side of the support part 222, an end of a support axis 221 is attached. The other end of the support axis 221 is arranged in the housing of the phantom retaining tool 200.

The phantom retaining tool 200 provides the actuators 201, 202 and 203 such as a stepper motor (pulse motor). The actuators 201, 202 and 203 operate independently of each other, based on an electric signal from the computer apparatus 4. As for a connection line that sends an electric signal to each of the actuators 201, 202 and 203, it is not shown in the figure.

The drive axis of the actuator 201 (e.g. an axis of rotation of a stepper motor) is in contact with a movement member 211, the form of which is having the Y-direction (vertical direction) as the longer direction. On each surface of the drive axis of the actuator 201 and the movement member 211, spiral grooves are formed. The drive axis of the actuator 201 and the moving member 211 are arranged such that the concavity and convexity of the grooves fit each other. An end of the movement member 211 (upper end in FIG. 14) is attached to the support axis 221. According to such a structure, the moving member 211 and the support axis 221 move integrally in the Y-direction depending on the rotation direction and the rotation angle of the drive axis of the actuator 201. Accordingly, the phantom 100 mounted in the phantom mounting part 223 moves in the Y-direction.

Similarly, the drive axis 202a of the actuator 202 (e.g. an axis of rotation of a stepper motor) is in contact with a movement member 212 with the X-direction (direction perpendicular to the Y-direction and Z-direction; horizontal direction) as the longer direction. On each surface of the drive axis 202a of the actuator 202 and the movement member 212, spiral grooves are formed. Thereby, the movement member 212 and the support axis 221 move integrally in the X-direction depending on the rotation direction and the rotation angle of the drive axis 202a, and the phantom 100 mounted on the phantom mounting part 223 moves in the X-direction.

The actuator 203 is fixed to the support part 222. The drive axis 203a (e.g. an axis of rotation of a stepper motor) of the actuator 203 passes through the neighborhood of the bottom head of the support part 222. The end of the drive axis 203a is inserted into a hole (not shown) in the phantom mounting part 223. On the surface of the drive axis 203a, spiral grooves are formed. Also, on the inner wall of the hole in the phantom mounting part 223, spiral grooves are formed. In the grooves of the drive axis 203a and the grooves of the hole, the concavity and convexity of the grooves fit each other.

The phantom mounting part 223 and the support part 222 are attached to each other by the mounting member 224 as mentioned above. On a rotation of the drive axis 203a of the actuator 203, due to the grooves being fitted to each other as mentioned above, the phantom mounting part 223 moves the mounting position with the mounting member 224 as the center of the movement relative to the drive axis 203a. Consequently, the cylinder axis J of the phantom 100 tilts in the vertical direction (Y-direction) relative to the Z-direction. The gradient corresponds to the tilt of the gantry 2.

Herein, the surface the support part 222 on the phantom mounting part 223 side tilts as mentioned. Accordingly, by rotating the drive axis 203a of the actuator 203 in a direction, the front side of the phantom 100 (the side which is not mounted in the phantom mounting part 223; left side of the page in FIG. 14) can be tilted upward, and by rotating the drive axis 203a in the opposite direction, the front side of the phantom 100 can be tilted downward. In addition, the phantom 100 tilts by the corresponding degree to the rotation angle of the drive axis 203a.

The rotation direction of the drive axis 203a of the actuator 203 can be switched by the control of the computer apparatus 4. Similarly, the rotation directions of the drive axis of the actuator 201 or the drive axis 202a of the actuator 202 can also be switched by the control of the computer apparatus 4.

If each actuator 201, 202 and 203 is a stepper motor, the computer apparatus 4 sends an electric signal with the pulse number corresponding to the desired rotation angle to the actuator 201-203. Wherein, the corresponding rotation angle of the drive axis to one pulse number is predetermined. The actuators 210-203 rotate the drive axes by the rotation angle corresponding to the pulse number of the signal sent by the computer apparatus 4. Accordingly, the phantom 100 can be moved to the desired distance in the X-direction or the Y-direction, as well as tilted by the desired gradient angle.

When the actuators 201-203 other than stepper motors are applied, by performing the control in accordance with the structures of the actuators 201-203, it is configured to move phantom 100 to the desired distance and tilt it by the desired gradient angle.

Then, the structure of a control system of the X-ray CT apparatus 1' in this embodiment will be described with reference to FIG. 15. The control system of the X-ray CT apparatus 1' is configured almost the same as the first embodiment (Refer to FIG. 3 and FIG. 4).

A retaining tool control part 54 is included in the apparatus control part 41 of the computer apparatus 4 of the X-ray CT apparatus 1'. The retaining tool control part 54 controls the operation of the phantom retaining tool 200. More specifically, the retaining tool control part 54 sends the signal mentioned above to each of the actuators 201-203 to move or tilt the phantom 100 by rotating the drive axis.

In FIG. 15, it is described that the signal from the retaining tool control part 54 is input directly into the phantom retaining tool 200, however, in practice, the signal is input into the phantom retaining tool 200 via the gantry 2 and the bed 3 as shown in the example in FIG. 13.

Action

Figure 16:
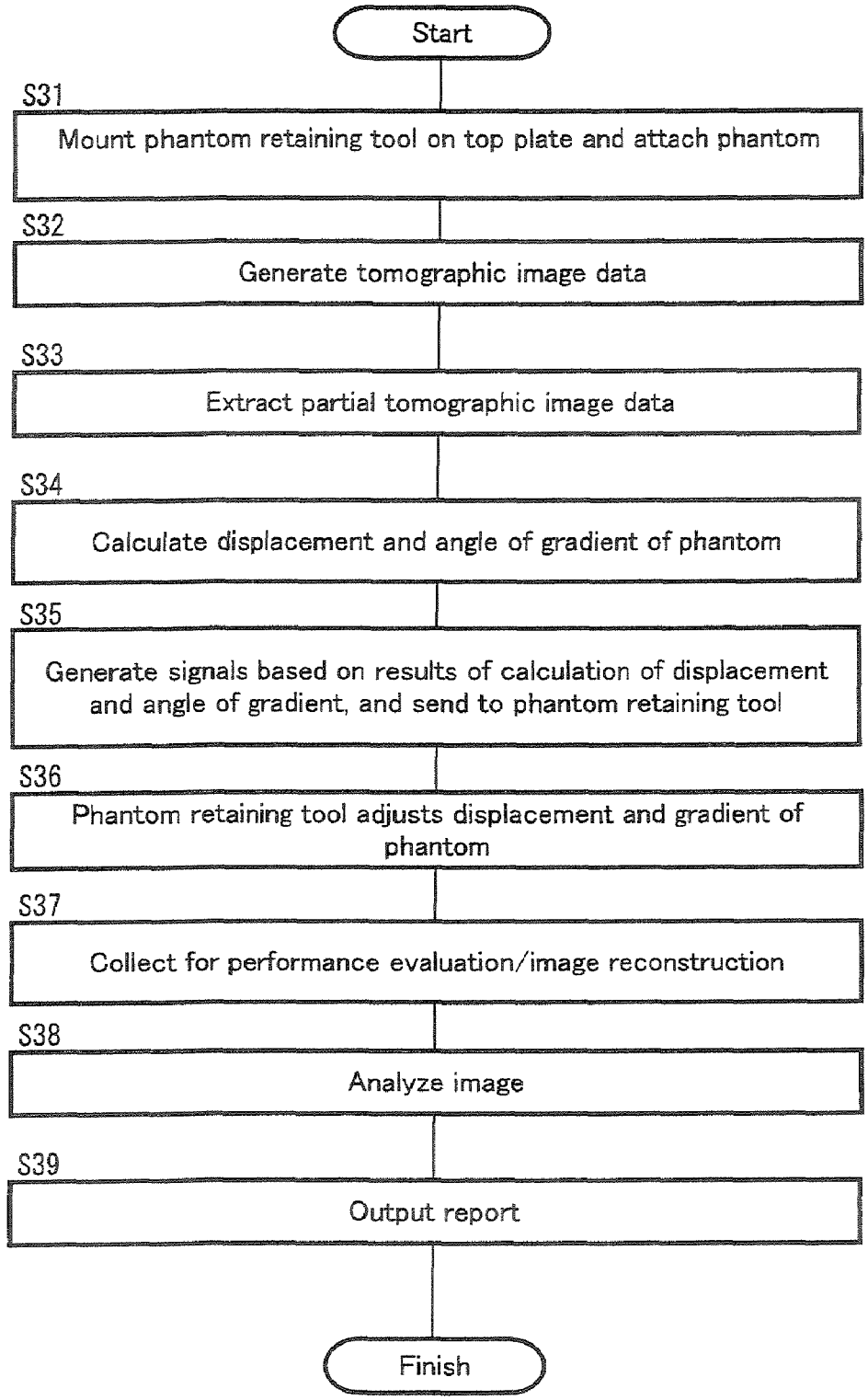
FIG. 16 is a flow chart showing an example of the action of the third embodiment of X-ray CT apparatus related to the invention.

The action of the X-ray CT apparatus 1' will be described with reference to the flow chart in FIG. 16. The detail of the calculation process for the displacement and the gradient angle of the phantom 100, which is described in the first and the second embodiments, are omitted in what follows.

First, on mounting the phantom retaining tool 200 on the top plate 31, the phantom 100 is mounted in the phantom mounting part 223 (S31). Then, by conducting a collection of the projection data of the phantom 100 and an image reconstruction, the tomographic image data of the phantom 100 is generated (S32). The housing extraction part 81 extracts a partial tomographic image data corresponding to the case 101 from the tomographic image data (S33). The calculation part 80 and the error processing part 90 analyze the partial tomographic image data to calculate the displacement in the X-direction, the displacement in the Y-direction and the gradient angle of the phantom 100 (S34). The calculation results are sent to the retaining tool control part 54 in the apparatus control part 41.

The retaining tool control part 54 generates a signal based on the calculation results of the displacement in the X-direction, the displacement in the Y-direction and the gradient angle, which is sent to the phantom retaining tool 200 (S35).

A specific example of this process will be described. At first, based on the calculation results of the displacement in the X-direction and the rotation angle of the drive axis 202a of the actuator 202 corresponding to one pulse, the retaining tool control part 54 derives the rotation direction of the drive axis 202a (moving direction in the X-direction) and the pulse number (moving distance), and generates a signal corresponding to the results. Then, the retaining tool control part 54 sends the signal together with the identification information for the identifying the actuator 202. By doing so, the signal is sent to the actuator 202.

The process of generating a signal based on the calculation result of the displacement in the Y-direction, and the process of sending the signal to the actuator 201, can be conducted in the same way.

The process of generating and sending a signal to control the actuator 203 will be described. Based on the calculation result of the rotation direction and the rotation angle of the drive axis 203a of the actuator 203 corresponding to one pulse (in other words, the gradient angle of the phantom 100 corresponding to one pulse), the retaining tool control part 54 derives the rotation direction and the pulse number of the drive axis 203a, and generates a signal corresponding to the results. Then the retaining tool control part 54 sends the signal together with the identification information of the actuator 203.

Each of the actuators 201-203 operates based on the signal from the retaining tool control part 54 and rotates the drive axis of each (S36). By doing so, the displacement of the phantom 100 in the X-direction or the Y-direction and even the gradient angle of the phantom 100 can be adjusted.

Then, the X-ray CT apparatus 1' collects projection data by X-radiating the phantom 100, as well as reconstructs the image of the phantom 100 (S37). The reconstructed image data is sent to the hospital server 1000 through LAN (refer to FIG. 11).

The hospital server 1000 analyzes the image data of the reconstructed image of the phantom 100, and conducts a performance evaluation on the X-ray CT apparatus 1' to generate a report (S38). The hospital server 1000 sends the generated report to the X-ray CT apparatus 1' through LAN. Herein, if the evaluation result is not good, the hospital server 1000 sends such a report as the evaluation result to the service server 2000 through WAN.

The X-ray CT apparatus 1' outputs the report received from the hospital server 1000 (S39). With that, the operation relating to the embodiment is completed. By referring to the output report, an operator of the X-ray CT apparatus 1', can perform various setting modifications of the X-ray CT apparatus 1' as appropriate.

Function and Advantage

The function and the advantage of the X-ray CT apparatus 1' in this embodiment will be described.

According to the X-ray CT apparatus 1', since it is configured to calculate the displacement in the X-direction as well as in the Y-direction and even the gradient angle of the phantom 100 mounted on the top plate 31, and move (in the X-direction or the Y-direction) or tilt the phantom 100, the operator is not required to perform the placement operation of the phantom 100 manually. Therefore, regardless of the skill of the operator, positioning of the phantom 100 can be done easily and quickly.

Furthermore, according to the X-ray CT apparatus 1', the positioning of the phantom 100 can be more accurate. In detail, as the second embodiment, as described above, adjusts the position of the phantom 100 by driving the top plate 31 or the gantry 2, the phantom 100 can be adjusted with at most the accuracy of the unit moving distance of the top plate 31 and with at most the accuracy of the unit gradient angle of the gantry 2. On the other hand, in this embodiment, by setting the unit rotation angle of the drive axes of the actuators 201-203 sufficiently small, the accuracy of the position adjustment for the phantom 100 may be improved. As a specific example, stepper motors with small rotation angles of the drive axes corresponding to one pulse may be used as the actuators 201-203.

Modified Embodiments

Regarding the embodiment of the X-ray CT apparatus 1', various modified embodiments will be described.

As described above, the X-ray CT apparatus 1' is configured to be able to automatically adjust all of the displacements in the X-direction as well as in the Y-direction and the gradient angle; however, it is sufficient only to be configured to be able to automatically adjust at least one of the three.

The X-ray CT apparatus 1' also adjusts the gradient of the phantom 100 in the vertical direction relative to the normal direction of the rotation plane of the gantry 2 (by the operation of the actuator 203). In this invention, it is possible for the configuration to be able to adjust the gradient of the phantom 100 to any direction, for example, adjusting the gradient of the phantom 100 in the horizontal direction relative to the normal direction of the rotation plane of the gantry 2. In this case, an actuator that corresponds to the adjustment direction of the gradient of the phantom 100 needs to be provided.

The X-ray CT apparatus 1' is also configured to automatically operate the phantom retaining tool 200; however, it is also possible to be configured to operate the phantom retaining tool 200 by an operator operating the input device 6, by displaying the displacement or the gradient of the phantom 100 on the monitor 5, as in the first embodiment.

Although omitted in the description of the motion of the X-ray CT apparatus 1', as in the first and the second embodiments, it is possible to output a warning message to the configuration when the position error of the phantom 100 is large.

Phantom Retaining Tool

The phantom retaining tool 200 of the X-ray CT apparatus 1' relates to an example of the "phantom retaining tool" of this invention. The phantom retaining tool 200 performs by being controlled by the apparatus control part 41 of the X-ray CT apparatus 1', and it includes the actuators 201-203 that move the phantom 100, retained on the top plate 31, in the vertical direction or the horizontal direction.

The apparatus control part 41 relates to an example of the "control device" of this invention. Each of the actuators 201 and 202 moves the phantom 100 in the vertical direction (Y-direction) and the horizontal direction (X-direction), h corresponding to an example of the "phantom drive unit". The actuator 203 serves as the "phantom gradient drive unit" that tilts the phantom 100 in the gradient direction with reference to the normal direction of the rotation plane of the gantry 2.

The normal direction of the rotation plane of the gantry 2 is identical with the Z-direction when the X-ray tube 22 and the X-ray detector 23 are arranged in the vertical plane. When the X-ray tube 22 and the X-ray detector 23 are not arranged in the vertical plane, the normal direction of the rotation plane of the gantry 2 is the direction perpendicular to the surface including the straight line connecting the X-ray tube 22 and the X-ray detector 23 (rotation plane). The "gradient direction with reference to the normal direction" means the gradient direction to the direction in which the gradient angle relative to said normal direction is varied.

By using such phantom retaining tool 200, it is possible to improve the accuracy of the positioning of the phantom 100. Additionally, instead of operating an operation portion such as a knob of the phantom retaining tool in the conventional way, it is possible to adjust the position of the phantom 100 by operating the input device 6, thereby the positioning of the phantom can be done easily and quickly.

Computer Program

The methods for positioning the phantom described in the first, second and third embodiments explained above, are implemented by the microprocessor of the computer apparatus 4 based on the computer program stored in such device as its hard disk drive. In particular, the apparatus control part 41 and the image processing part 42 performs according to the computer program.

Those computer programs can be stored in any storage media. The computer can read the computer program from the storage media. Any storage media, which is configured to be able to store data by any physical method including an electrical method, magnetic method and optical method, can be used. The specific examples of those storage media are diskette, CD-ROM, CD-R, CD-RW, DVD-ROM, DVD-R, DVD-RW, DVD-RAM, MO and various memory cards.

A configuration to store the computer program in a server or a storage media on a network such as the Internet and LAN to be used by the computer apparatus 4 by accessing via the network is also possible.

The configurations described above are merely illustrative for the practice of the invention, and therefore, any modification can be made without departing from the scope of the invention.

What is claimed is:

1. An X-ray CT apparatus, comprising:
   a top plate on which a phantom with a cylindrical housing is placed;
   an X-ray generator;
   an X-ray detector for X-rays transmitted through the phantom placed on the top plate;
   a rotational drive unit rotating said X-ray generator and said X-ray detector;
   a storage device storing, in advance, coordinates of the center of rotation by the rotational drive unit;
   tomographic image data generator for generating tomographic image data for the phantom, based on the results of detecting X-rays by the X-ray detector;
   an extraction unit extracting partial tomographic image data corresponding to the housing of the phantom from the generated tomographic image data;
   a circle center calculation unit calculating the coordinates of the center of a circle passing through three different points in the extracted partial tomographic image data;
   a first displacement calculation unit calculating displacement of the cylinder axis of the phantom relative to the center of rotation in a horizontal direction which is perpendicular to a body axis of the phantom, based on the calculated coordinates of the center of the circle and the stored coordinates of the center of rotation;
   an error calculation unit calculating error of different multiple points in the extracted partial tomographic image data relative to the circle;
   a determination unit determining whether the calculated error exceeds a predetermined value;
   an ellipse center calculation unit calculating the coordinates of the center of an ellipse passing through four different points in the extracted partial tomographic image data when the error was determined to exceed the predetermined value;
   a second displacement calculation unit calculating displacement of the cylinder axis of the phantom relative to the center in the horizontal direction which is perpendicular to the body axis of the phantom, based on the calculated coordinates of the center of the ellipse and the stored coordinates of the center of rotation;
   a radius calculation unit calculating both the horizontal radius and the vertical radius of the ellipse when the error was determined to exceed the predetermined value;
   a gradient angle calculation unit calculating the angle of gradient of the cylinder axis of the phantom relative to the normal direction of the rotation plane of the rotation, based on the calculated horizontal radius and the vertical direction;
   a gradient drive unit tilting the X-ray generator and the X-ray detector integrally, based on the calculated angle of gradient, so as to align the normal direction of the rotation plane with the cylinder axis of the phantom; and
   a top plate drive unit moving the top plate in the horizontal direction which is perpendicular to the body axis of the phantom to align the cylinder axis of the phantom with the center of rotation, based on the displacement in the horizontal direction which is perpendicular to the body axis of the phantom calculated by the first displacement calculation unit, when the error was determined not to exceed the predetermined value by the determination unit, and moving the top plate in the horizontal direction which is perpendicular to the body axis of the phantom to align the cylinder axis of the phantom with the center of rotation, based on the displacement in the horizontal direction which is perpendicular to the body axis of the phantom calculated by the second displacement calculation unit, when the error was determined to exceed the predetermined value.

\* \* \* \* \*